(12) United States Patent
Green et al.

(10) Patent No.: US 8,278,306 B2
(45) Date of Patent: Oct. 2, 2012

(54) C-MET PROTEIN KINASE INHIBITORS

(75) Inventors: Jeremy Green, Waltham, MA (US);
Jingrong Cao, Newton, MA (US); Upul Keerthi Bandarage, Lexington, MA (US); Jon H. Come, Cambridge, MA (US); Craig Marhefka, Rockville, MD (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/253,322

(22) Filed: Oct. 5, 2011

(65) Prior Publication Data
US 2012/0065213 A1   Mar. 15, 2012

Related U.S. Application Data

(62) Division of application No. 11/801,686, filed on May 10, 2007, now Pat. No. 8,058,271.

(60) Provisional application No. 60/799,914, filed on May 12, 2006.

(51) Int. Cl.
*A61K 31/5377* (2006.01)
*A61K 31/496* (2006.01)
*A61K 31/4545* (2006.01)
*A61K 31/4436* (2006.01)
*C07D 413/04* (2006.01)
*C07D 401/14* (2006.01)
*C07D 417/04* (2006.01)

(52) U.S. Cl. ............... 514/253.01; 514/237.2; 514/318; 514/342; 544/124; 544/360; 546/194; 546/270.4

(58) Field of Classification Search ................ 544/124, 544/360; 546/194, 270.4; 514/237.2, 253.01, 514/318, 342
See application file for complete search history.

(56) References Cited

FOREIGN PATENT DOCUMENTS

| WO | 2004041813 | 5/2004 |
| WO | 2005074642 | 8/2005 |
| WO | 2005100342 | 10/2005 |

OTHER PUBLICATIONS

PCT/US2007/011285 International Search Report.

*Primary Examiner* — Patricia Morris
(74) *Attorney, Agent, or Firm* — Daniel A. Pearson

(57) ABSTRACT

Described herein are compounds that are useful as ROCK inhibitors. These compounds, and pharmaceutically acceptable compositions thereof, are useful for treating or lessening the severity of a variety of disorders, including cardiovascular, inflammatory, neurological, or proliferative diseases or disorders.

16 Claims, No Drawings

C-MET PROTEIN KINASE INHIBITORS

CROSS-REFERENCE TO RELATED APPLICATIONS

The present application is a divisional application of U.S. patent application Ser. No. 11/801,686 filed May 10, 2007, now U.S. Pat. No. 8,058,271 which claims the benefit, under 35 U.S.C. §119, to U.S. Provisional Application No. 60/779,914, filed May 12, 2006, the entire disclosures of each of which are incorporated herein by reference.

TECHNICAL FIELD OF THE INVENTION

The present invention relates to heteroaryl compounds that are protein kinase inhibitors, compositions containing such compounds, and methods for their use. The compounds and compositions of the invention are useful for treating cardiovascular, inflammatory, neurological, or proliferative diseases or disorders.

BACKGROUND OF THE INVENTION

One kinase family of interest is Rho-associated coiled-coil forming protein serine/threonine kinase (ROCK), which is believed to be an effector of Ras-related small GTPase Rho. The ROCK family includes p160ROCK (ROCK-1), ROKα/Rho-kinase/ROCK-II, protein kinase PKN, citron, and citron kinase. The ROCK family of kinases have been shown to be involved in a variety of functions including Rho-induced formation of actin stress fibers and focal adhesions and in down-regulation of myosin phosphatase, platelet activation, aortic smooth muscle contraction by various stimuli, thrombin-induced responses of aortic smooth muscle cells, hypertrophy of cardiomyocytes, bronchial smooth muscle contraction, smooth muscle contraction and cytoskeletal reorganization of non-muscle cells, activation of volume-regulated anion channels, neurite retraction, neutrophil chemotaxis, wound healing, tumor invasion and cell transformation. More specifically, ROCK has been implicated in various diseases and disorders including hypertension, cerebral vasospasm, coronary vasospasm, bronchial asthma, pre-term labor, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, benign prostatic hyperplasia and atherosclerosis.

U.S. Patent Application Publication No. 20040122016 describes several pyridylthiazole and pyridylthiofuran inhibitors of ROCK. The development of other inhibitors of ROCK kinase would be useful for the treatment of diseases and disorders associated with the ROCK kinase pathway.

SUMMARY OF THE INVENTION

The present invention features compounds having the formula:

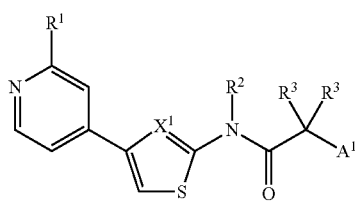

I or a pharmaceutically acceptable salt or prodrug thereof, where $R^1$, $R^2$, $R^3$, $X^1$, and $A^1$ are as defined herein. These compounds and pharmaceutically acceptable compositions or prodrugs thereof are useful for treating or lessening the severity of a variety of ROCK-mediated diseases or disorders disorders, especially cardiovascular, inflammatory, neurological, or proliferative diseases or disorders. In addition, these compounds are useful because they inhibit cytochrome P450 only at high concentrations.

DETAILED DESCRIPTION OF THE INVENTION

Compounds of the Invention

As used herein, the following definitions shall apply unless otherwise indicated. As described herein, compounds or classes of compounds of the invention may optionally be substituted with one or more substituents, such as, for example, one, two, three, four, or five substituents. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as hydrogen, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Occasionally, the location of aryl, heterocyclyl, or heteroaryl ring substitutions will be defined by position. In such examples, unless otherwise indicated, the 1-position of the ring is that position that is bonded to the remainder of the molecule. The other positions are numbered according to priority designations defined by standard IUPAC nomenclature.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one to five of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one to five units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like. The term "alkenyl," as used herein, represents monovalent straight or branched chain hydrocarbon group containing one to five carbon-carbon double bonds. The term "alkynyl," as used herein, represents a monovalent straight or branched chain hydrocarbon group containing one to five carbon-carbon triple bonds.

The term "alkylidene chain" refers to a straight or branched carbon chain that may be fully saturated or have one or more units of unsaturation and has two points of connection to the rest of the molecule.

The term "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one to five units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," or "heterocyclic" as used herein refers to a monocyclic, bicyclic, or tricyclic ring system in which one to five ring members are an independently selected heteroatom and that is completely saturated or that contains one to five units of unsaturation, but which is not aromatic, that has a single point of attachment to the rest of the molecule. In some embodiments, the "heterocycle," "heterocyclyl," or "heterocyclic" group has three to fourteen ring members in which one to five ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one to five of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated," as used herein, means that a moiety has one to five units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" means alkyl, alkenyl, or alkoxy, as the case may be, substituted with one to five halogen atoms. The term "halogen" means F, Cl, Br, or I.

The term "aryl" used alone or as part of a larger moiety as in "aralkyl," "aralkoxy," or "aryloxyalkyl," refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one to five heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one to five substituents. Suitable substituents on the unsaturated carbon atom of an aryl or heteroaryl group include: halogen; —R°; —OR°; —SR°; 1,2-methylenedioxy; 1,2-ethylenedioxy; phenyl (Ph), optionally substituted with R°; —O(Ph), optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —B(OR°)$_2$; —OC(O)N(R°)$_2$; —OC(O)R°; —C(O)N(OR°)R°; —C(NOR°)R°; —S(O)$_2$R°; —S(O)$_2$OR°; —S(O)$_2$N(R°)$_2$; —S(O)R°; —NR°S(O)$_2$N (R°)₂; —NR°S(O)₂R°; —N(OR°)R°; —C(=NH)—N(R°)₂; —(CH₂)₀₋₂NHC(O)R°; -L-R°; -L-N(R°)₂; -L-SR°; -L-OR°; -L-(C₃₋₁₀ cycloaliphatic), -L-(C₆₋₁₀ aryl), -L-(5-10 membered heteroaryl), -L-(5-10 membered heterocyclyl), oxo, C₁₋₄ haloalkoxy, C₁₋₄ haloalkyl, -L-NO₂, -L-CN, -L-OH, -L-CF₃; or two substituents, on the same carbon or on different carbons, together with the carbon or intervening carbons to which they are bound, form a 5-7 membered saturated, unsaturated, or partially saturated ring, wherein L is a C₁₋₆ alkylene group in which up to three methylene units are replaced by —NH—, —NR°—, —O—, —S—, —C(O)O—, —OC(O)—, —C(O)C(O)—, —C(O)—, —C(O)NH—, —C(O)NR°—, —C(=N—CN), —NHC(O)—, —NR°C(O)—, —NHC(O)O—, —NR°C(O)O—, —S(O)₂NH—, —S(O)₂NR°—, —NHS(O)₂—, —NR°S(O)₂—, —NHC(O)NH—, —NR°C(O)NH—, —NHC(O)NR°—, —NR°C(O)NR°, —OC(O)NH—, —OC(O)NR°—, —NHS(O)₂NH—, —NR°S(O)₂NH—, —NHS(O)₂NR°—, —NR°S(O)₂NR°—, —S(O)—, or —S(O)₂—, and wherein each occurrence of R° is independently selected from hydrogen, optionally substituted C₁₋₆ aliphatic, an unsubstituted 5- to 6-membered heteroaryl or heterocyclic ring, phenyl, or —CH₂(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Optional substituents on the aliphatic group of R° are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, C(O)OH, C(O)O(C₁₋₄ aliphatic), O(halo(C₁₋₄ aliphatic)), or halo(C₁₋₄ aliphatic), wherein each of the foregoing C₁₋₄ aliphatic groups of R° is unsubstituted.

In some embodiments, an aliphatic or heteroaliphatic group, or a non-aromatic heterocyclic ring may contain one to five substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHC(O)O(alkyl), =NNHS(O)₂(alkyl), or =NR*, where each R* is independently selected from hydrogen or an optionally substituted C₁₋₆ aliphatic. Optional substituents on the aliphatic group of R* are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, C(O)OH, C(O)O(C₁₋₄ aliphatic), O(halo-C₁₋₄ aliphatic), and halo(C₁₋₄ aliphatic), where each of the foregoing C₁₋₄ aliphatic groups of R* is unsubstituted.

In some embodiments, optional substituents on the nitrogen of a non-aromatic heterocyclic ring include —R⁺, —N(R⁺)₂, —C(O)R⁺, —C(O)OR⁺, —C(O)C(O)R⁺, —C(O)CH₂C(O)R⁺, —S(O)₂R⁺, —S(O)₂N(R⁺)₂, —C(=S)N(R⁺)₂, —C(=NH)—N(R⁺)₂, or —NR⁺S(O)₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R⁺, on the same substituent or different substituents, taken together with the atom(s) to which each R⁺ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R⁺ are selected from NH₂, NH(C₁₋₄ aliphatic), N(C₁₋₄ aliphatic)₂, halogen, C₁₋₄ aliphatic, OH, 0(C₁₋₄ aliphatic), NO₂, CN, C(O)OH, C(O)O(C₁₋₄ aliphatic), O(halo(C₁₋₄ aliphatic)), or halo (C₁₋₄ aliphatic), wherein each of the foregoing C₁₋₄ aliphatic groups of R⁺ is unsubstituted.

As detailed above, in some embodiments, two independent occurrences of R° (or R⁺, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

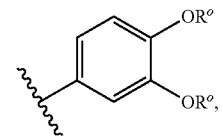

these two occurrences of R° are taken together with the oxygen atoms to which they are bound to form a fused 6-membered oxygen containing ring:

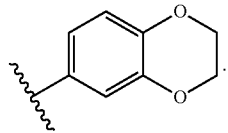

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —C(O)O—, —OC(O)—, —C(O)C(O)—, —C(O)—, —C(O)NR—, —C(=N—CN), —NRC(O)—, —NRC(O)O—, —S(O)₂NR—, —NRS(O)₂—, —NRC(O)NR—, —OC(O)NR—, —NRS(O)₂NR—, —S(O)—, or —S(O)₂—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to a hydrogen on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, Figure a represents possible substitution in any of the positions shown in Figure b.

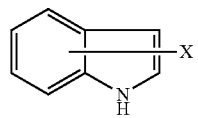

FIG. a

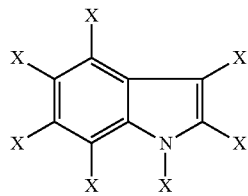

FIG. b

This also applies to multiple ring systems fused to optional ring systems (which would be represented by dotted lines). For example, in Figure c, X is an optional substituent both for ring A and ring B.

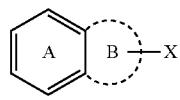

FIG. c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

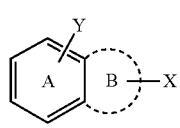

FIG. d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate forming groups such as benzyloxycarbonyl, 4-chlorobenzyloxycarbonyl, 4-methoxybenzyloxycarbonyl, 4-nitrobenzyloxycarbonyl, 2-nitrobenzyloxycarbonyl, 4-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I, or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic (C$_1$-C$_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, all tautomeric forms of the compounds of the invention are within the scope of the invention. Additionally, unless otherwise stated, structures depicted herein are also meant to include compounds that differ only in the presence of one to five isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

In a first aspect, the present invention features a compound having the formula:

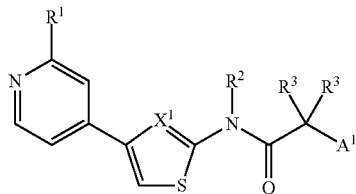

or a pharmaceutically acceptable salt or prodrug thereof, wherein:

$R^1$ is halogen, —CN, —NO$_2$, —NR$_2$, —OR, —SR, or an optionally substituted C$_{1-4}$ aliphatic or C$_{3-6}$ cycloaliphatic;

$R^2$ is hydrogen or C$_{1-3}$ aliphatic;

each $R^3$ is, independently, hydrogen, halogen, —NR$_2$, —OR, —SR, or an optionally substituted C$_{1-4}$ aliphatic group or C$_{3-6}$ cycloaliphatic group, or two $R^3$, taken together with the intervening carbon atom, form an optionally substituted 3-6 membered cycloaliphatic or heterocyclyl ring having 1-2 heteroatoms selected from nitrogen, oxygen, or sulfur;

$X^1$ is CR$^4$ or N, wherein $R^4$ is hydrogen, halogen, —C(O)R, —C(S)R, —C(O)N(R)$_2$, —C(S)N(R)$_2$, —CN, —NO$_2$, or an optionally substituted C$_{1-4}$ aliphatic group;

$A^1$ is a phenyl ring or a 5-6 membered heteroaryl ring having 1-3 heteroatoms independently selected from nitrogen, oxygen, or sulfur, wherein said phenyl or heteroaryl ring is optionally substituted with 1-5 independent occurrences of TR$^5$, wherein two TR$^5$ groups are optionally taken together to form methylenedioxy or ethylenedioxy;

T is a bond or a C$_1$-C$_6$ alkylidene chain, wherein up to two methylene units of T are optionally and independently replaced by —NR'—, —S—, —O—, —C(S)—, —C(O)O—, —OC(O)—, —C(O)—, —C(O)C(O)—, —C(O)NR'—, —NR'C(O)—, —NR'C(O)O—, —S(O)$_2$NR'—, —NR'S(O)$_2$—, —C(O)NR'NR'—, —NR'C(O)NR'—, —OC(O)NR'—, —NR'NR'—, —NR'S(O)$_2$NR'—, —S(O)—, —S(O)$_2$—, —P(O)—, —P(O)$_2$—, —P(O)R;

each $R^5$ is independently $R^a$, halogen, —NO$_2$, or —CN;

each occurrence of $R^a$ is, independently, hydrogen, an optionally substituted moiety selected from a C$_{1-4}$ aliphatic group, a C$_{3-6}$ cycloaliphatic group, a C$_{1-4}$ haloaliphatic group, a 6-10 membered mono- or bicyclic aryl ring, a 3-10 membered mono- or bicyclic cycloaliphatic ring, or a 5-14 membered mono- or bicyclic heteroaryl or heterocyclyl ring having 1-5 heteroatoms independently selected from nitrogen, oxygen, or sulfur, or wherein $R^a$, R', and an intervening nitrogen atom together form an optionally substituted 5-6 membered heterocyclic or heteroaryl ring optionally having 1-2 additional heteroatoms selected from nitrogen, oxygen, or sulfur; each optionally substituted group or ring is, independently, optionally substituted with 1-5 substituents independently selected from C$_{1-4}$ aliphatic, C$_{3-6}$ cycloaliphatic, C$_{1-4}$ haloaliphatic, halogen, —OR", —OC(O)N(R")$_2$, —OC(O)R", —OC(O)OR", —NO$_2$, —N(R")$_2$, —NR"C(O)R", —NR"C(S)R", —NR"C(O)N(R")$_2$, —NR"C(S)N(R")$_2$, —NR"C(O)OR", —NR"NR"C(O)R", —NR"NR"C(O)N(R")$_2$, —NR"NR"C(O)OR", —NR"S(O)$_2$N(R")$_2$, —NR"S(O)$_2$R", —N(OR")R", —CN, C(O)OR", —C(O)R", —C(S)R", —C(O)N(R")$_2$, —C(S)N(R")$_2$, —OC(O)N(R")$_2$, —OC(O)R", —C(O)N(OR")R", —C(=NOR")R", —C(=NH)—N(R")$_2$, —SR", —SC(O)R", —SC(S)R", —S(O)R", —S(O)$_2$R", —S(O)$_2$OR", or —S(O)$_2$N(R")$_2$;

each occurrence of R is, independently, hydrogen, a C$_{1-4}$ aliphatic group, a C$_{3-6}$ cycloaliphatic group, —(CH$_2$)$_{1-2}$Ph, —CH=CHPh, or a C$_{1-4}$ haloaliphatic group, or two R groups and an intervening nitrogen atom together form an optionally substituted 5-6 membered heterocyclic or heteroaryl ring optionally having 1-2 additional heteroatoms selected from nitrogen, oxygen, or sulfur;

each occurrence of R' is, independently, hydrogen, a C$_{1-4}$ aliphatic group, a C$_{3-6}$ cycloaliphatic group, —(CH$_2$)$_{1-2}$Ph, —CH=CHPh, or a C$_{1-4}$ haloaliphatic group, or two R' groups and an intervening nitrogen atom together form an optionally substituted 5-6 membered heterocyclic or heteroaryl ring optionally having 1-2 additional heteroatoms selected from nitrogen, oxygen, or sulfur; and each occurrence of R" is, independently, hydrogen, a C$_{1-4}$ aliphatic group, a C$_{3-6}$ cycloaliphatic group, —(CH$_2$)$_{1-2}$Ph, —CH=CHPh, or a C$_{1-4}$ haloaliphatic group, or two R" groups and an intervening nitrogen atom together form an optionally substituted 5-6 membered heterocyclic or heteroaryl ring optionally having 1-2 additional heteroatoms selected from nitrogen, oxygen, or sulfur.

In one embodiment, $R^2$ is hydrogen.

In another embodiment, $A^1$ is a phenyl ring or a 5-6 membered heteroaryl ring having 1-2 heteroatoms independently selected from nitrogen, oxygen, or sulfur, wherein said phenyl or heteroaryl ring is optionally substituted with 1-3 independent occurrences of TR$^5$, wherein two TR$^5$ groups are optionally taken together to form methylenedioxy or ethylenedioxy.

Examples of compounds of formula I wherein $A^1$ is a phenyl ring include compounds having the formula:

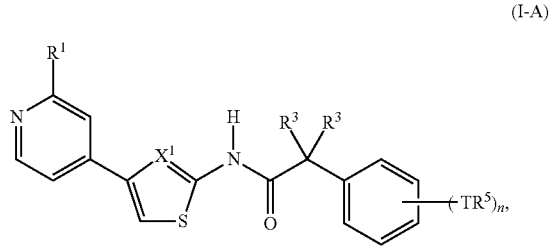

(I-A)

where $R^1$ is C$_{1-4}$ aliphatic, halogen, —NR$_2$, —OR, or —SR;

each T is, independently, a bond or a C$_1$-C$_6$ alkylidene chain, wherein up to two methylene units of T are optionally and independently replaced by —NR'—, —S—, —O—, —C(O)NR'—, —NR'C(O)—, —NR'C(O)O—, —S(O)$_2$NR'—, —NR'S(O)$_2$—, —NR'C(O)NR'—, —OC(O)NR'—, or —NR'S(O)$_2$NR'—, or two TR$^5$ groups are optionally taken together to form methylenedioxy or ethylenedioxy;

each $R^5$ is, independently, $R^a$ or halogen; and n is 1 to 3.

In one embodiment for any compound of formula I or I-A, one of -TR$^5$ is at the 3-position. In some examples, -TR$^5$ at the 3-position is chloro, fluoro, —OH, optionally substituted C$_{1-4}$ alkoxy, —NHS(O)$_2$R$^a$, —S(O)$_2$NRR$^a$, or two TR$^5$ groups at the 3 and 4 positions together are methylenedioxy.

In another embodiment for any compound of formula I or I-A, $R^1$ is halogen, such as, for example, chloro or fluoro; —NR$_2$, such as, for example, NH$_2$, NHCH$_3$, N(CH$_3$)$_2$, NHCH$_2$CH$_3$, or NHCH$_2$Ph; —OR, such as, for example, OCH$_3$ or OCH$_2$CH$_3$; or an optionally substituted C$_{1-4}$ aliphatic group, such as, for example, CH$_3$ or CH$_2$CH$_3$.

In yet another embodiment for any compound of formula I or I-A, each $R^3$ is, independently, hydrogen, halogen, $-NR'''_2$, $-OR'''$, $-SR'''$, or a $C_{1-4}$ aliphatic group, wherein each $R'''$ is, independently, hydrogen or a $C_{1-4}$ aliphatic group. Examples include those in which $R^3$ is hydrogen, chloro, fluoro, or $-OH$.

For some compounds of formula I or I-A, $X^1$ is $CR^4$, wherein $R^4$ is hydrogen or a $C_{1-4}$ aliphatic group. For other compounds of formula I or I-A, $X^1$ is N.

In another aspect, the invention features a compound selected from the list of compounds in Table 1.

TABLE 1

| Compound No. | Structure |
|---|---|
| 1 | 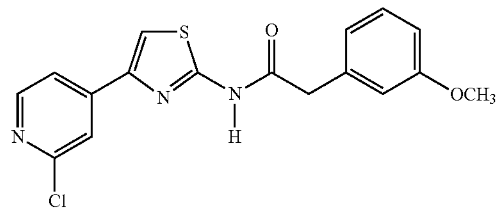 |
| 2 | 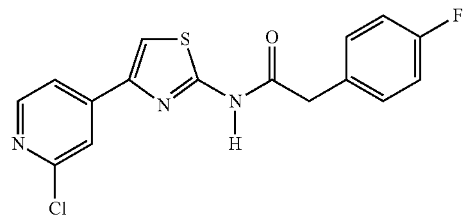 |
| 3 | 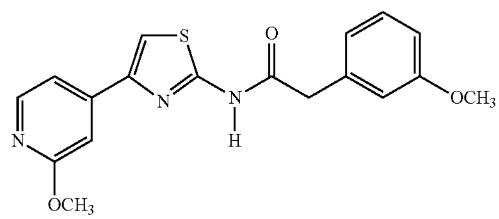 |
| 4 | 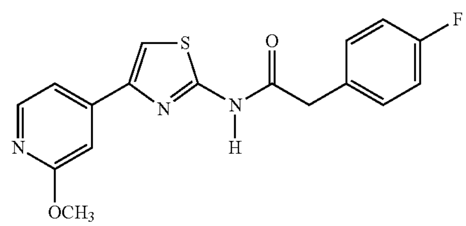 |
| 5 | 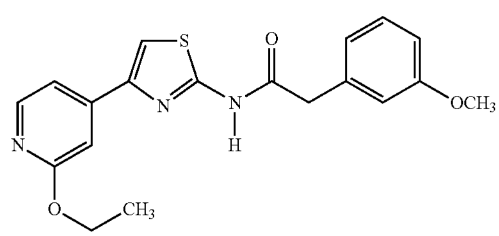 |
| 6 | 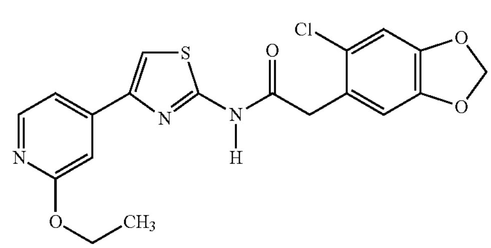 |

TABLE 1-continued

| Compound No. | Structure |
| --- | --- |
| 7 | 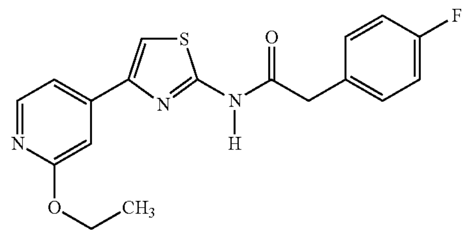 |
| 8 | 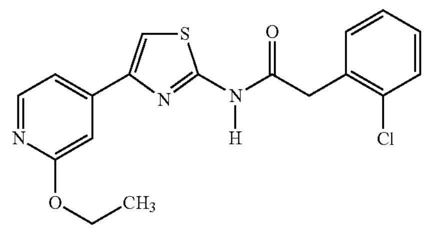 |
| 9 | 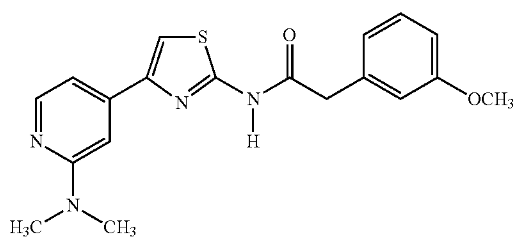 |
| 10 | 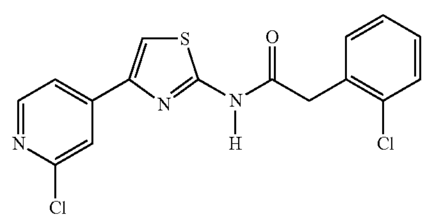 |
| 11 | 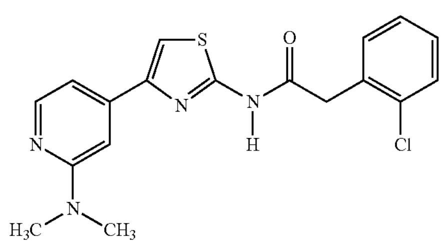 |
| 12 | 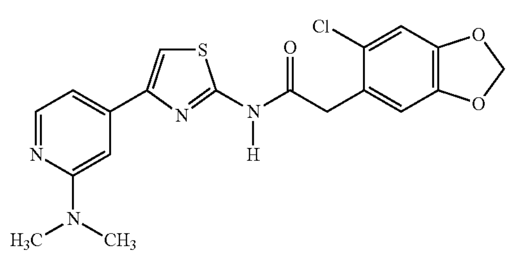 |

TABLE 1-continued

| Compound No. | Structure |
|---|---|
| 13 | 2-(3-methoxyphenyl)-N-[4-(2-fluoropyridin-4-yl)thiazol-2-yl]acetamide |
| 14 | 2-(3-methoxyphenyl)-N-[4-(2-benzylaminopyridin-4-yl)thiazol-2-yl]acetamide |
| 15 | 2-(3-methoxyphenyl)-N-[4-(2-ethylaminopyridin-4-yl)thiazol-2-yl]acetamide |
| 16 | 2-(2,4-difluorophenyl)-N-[4-(2-aminopyridin-4-yl)thiazol-2-yl]acetamide |
| 17 | 2-(6-chloro-benzo[1,3]dioxol-5-yl)-N-[4-(2-aminopyridin-4-yl)thiazol-2-yl]acetamide |
| 18 | 2-(3-methoxyphenyl)-N-[4-(2-aminopyridin-4-yl)thiazol-2-yl]acetamide |

TABLE 1-continued
| Compound No. | Structure |
|---|---|
| 19 | 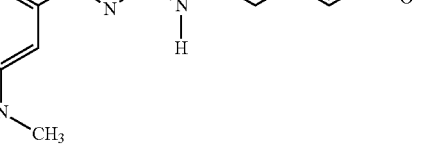 |
| 20 | 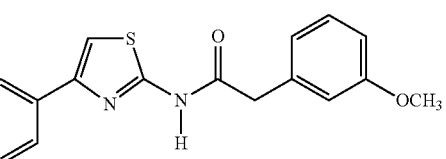 |
| 21 | 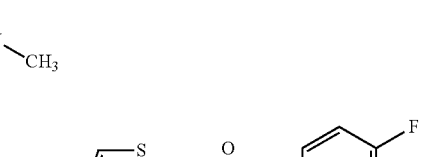 |
| 22 | 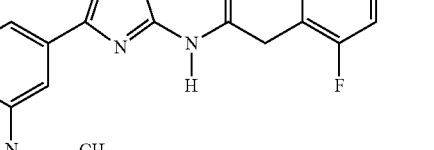 |
| 23 | 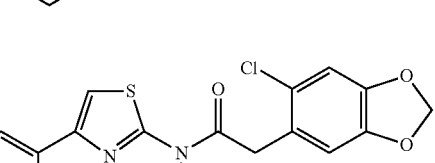 |
| 24 | 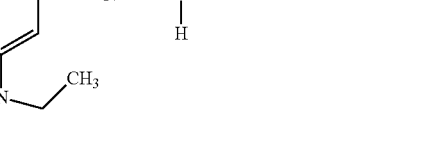 |

TABLE 1-continued

| Compound No. | Structure |
|---|---|
| 25 | 4-(pyridin-4-yl with 2-(benzylamino))-thiazol-2-yl N-[2-(2,4-difluorophenyl)acetamide] |
| 26 | 4-(pyridin-4-yl with 2-(benzylamino))-thiazol-2-yl N-[2-(6-chlorobenzo[d][1,3]dioxol-5-yl)acetamide] |
| 27 | 4-(2-aminopyridin-4-yl)-thiazol-2-yl N-[2-(2-chlorophenyl)acetamide] |
| 28 | 4-(2-(methylamino)pyridin-4-yl)-thiazol-2-yl N-[2-(2-chlorophenyl)acetamide] |
| 29 | 4-(2-(ethylamino)pyridin-4-yl)-thiazol-2-yl N-[2-(2-chlorophenyl)acetamide] |
| 30 | 4-(2-methylpyridin-4-yl)-thiazol-2-yl N-[2-(2,4-difluorophenyl)acetamide] |

TABLE 1-continued
| Compound No. | Structure |
|---|---|
| 31 | 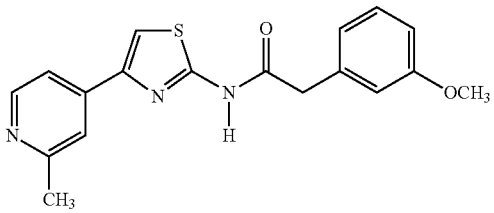 |
| 32 | 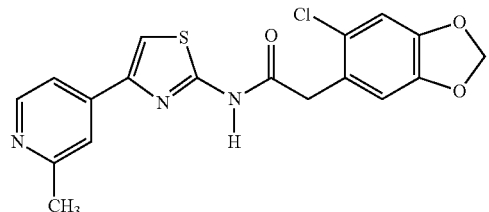 |
| 33 | 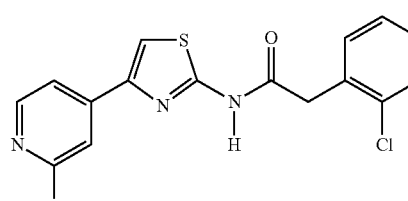 |
| 34 | 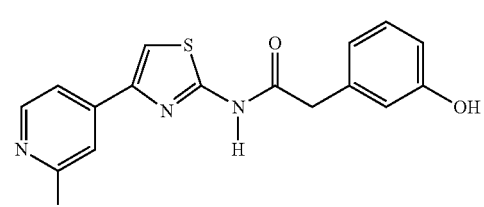 |
| 35 | 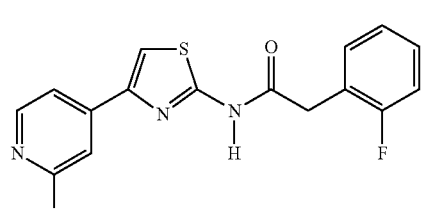 |
| 36 | 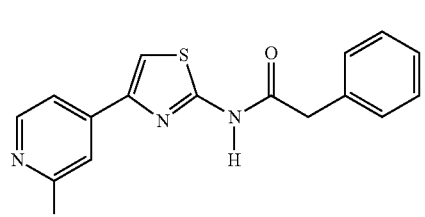 |
| 37 | 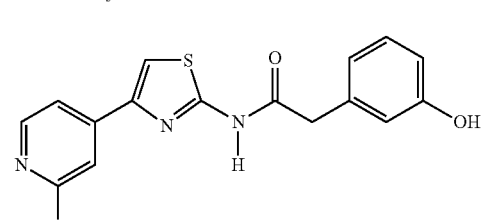 |

TABLE 1-continued
| Compound No. | Structure |
|---|---|
| 38 | 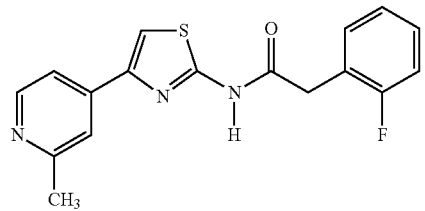 |
| 39 | 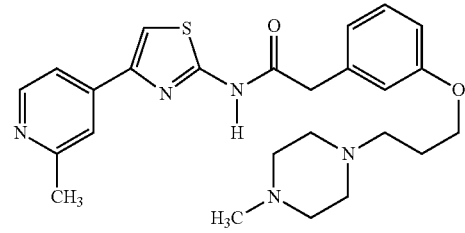 |
| 40 | 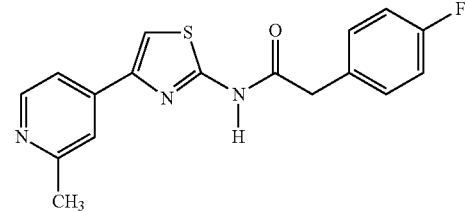 |
| 41 | 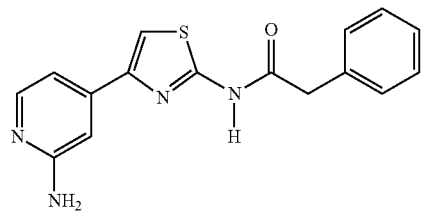 |
| 42 | 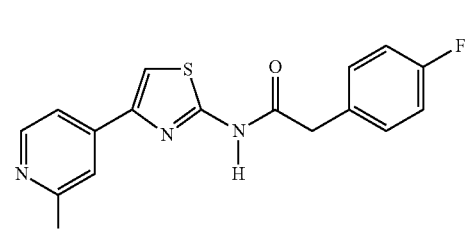 |
| 43 | 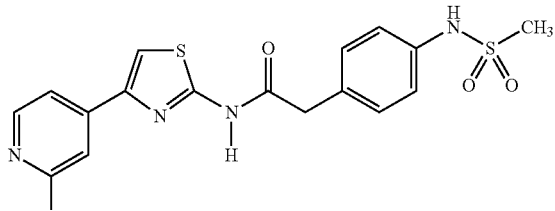 |

TABLE 1-continued

| Compound No. | Structure |
|---|---|
| 44 | 2-(4-(methylsulfonamido)phenyl)-N-(4-(2-methylpyridin-4-yl)thiazol-2-yl)acetamide |
| 45 | 2-(3-(3-(4-methylpiperazin-1-yl)propoxy)phenyl)-N-(4-(2-aminopyridin-4-yl)thiazol-2-yl)acetamide |
| 46 | N-(4-(2-chloropyridin-4-yl)thiazol-2-yl)-2-(2-fluorophenyl)acetamide |
| 47 | N-(4-(2-chloropyridin-4-yl)thiazol-2-yl)-2-(2,4-difluorophenyl)acetamide |
| 48 | N-(4-(2-chloropyridin-4-yl)thiazol-2-yl)-2-(3-hydroxyphenyl)acetamide |
| 49 | N-(4-(2-chloropyridin-4-yl)thiazol-2-yl)-2-(6-chlorobenzo[d][1,3]dioxol-5-yl)acetamide |
| 50 | N-(4-(2-chloropyridin-4-yl)thiazol-2-yl)-2-phenylacetamide |

TABLE 1-continued

| Compound No. | Structure |
|---|---|
| 51 | 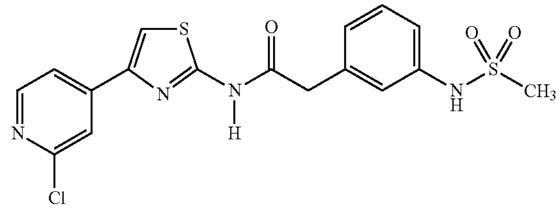 |
| 52 | 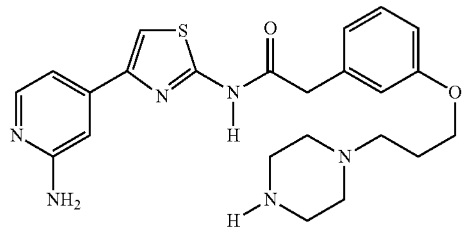 |
| 53 | 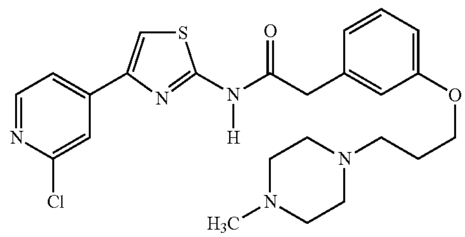 |
| 54 | 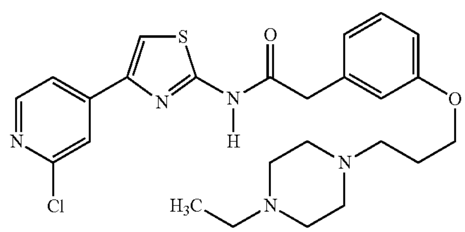 |
| 55 | 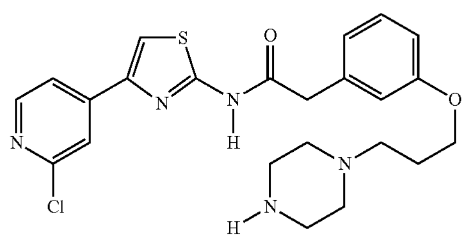 |
| 56 | 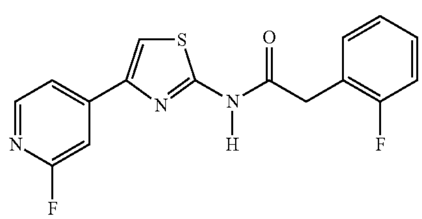 |
| 57 | 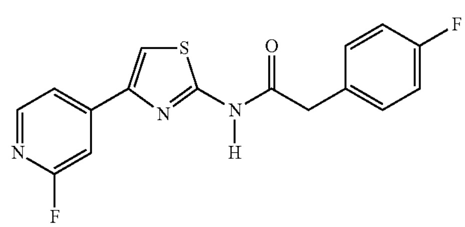 |

TABLE 1-continued

| Compound No. | Structure |
|---|---|
| 58 | 2-(2,4-difluorophenyl)-N-[4-(2-fluoropyridin-4-yl)thiazol-2-yl]acetamide |
| 59 | N-[4-(2-fluoropyridin-4-yl)thiazol-2-yl]-2-[3-(methylsulfonylamino)phenyl]acetamide |
| 60 | N-[4-(2-fluoropyridin-4-yl)thiazol-2-yl]-2-{3-[3-(4-methylpiperazin-1-yl)propoxy]phenyl}acetamide |
| 61 | N-[4-(2-fluoropyridin-4-yl)thiophen-2-yl]-2-(3-methoxyphenyl)acetamide |
| 62 | N-[4-(2-chloropyridin-4-yl)thiophen-2-yl]-2-(3-methoxyphenyl)acetamide |
| 63 | N-[4-(2-chloropyridin-4-yl)thiophen-2-yl]-2-[3-(methylsulfonylamino)phenyl]acetamide |
| 64 | N-[4-(2-aminopyridin-4-yl)thiophen-2-yl]-2-(3-methoxyphenyl)acetamide |

TABLE 1-continued

| Compound No. | Structure |
|---|---|
| 65 | 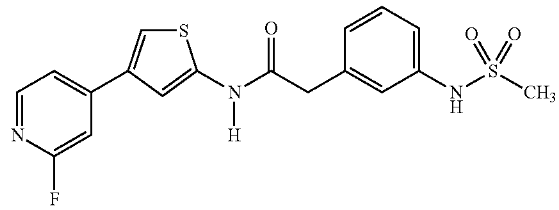 |
| 66 | 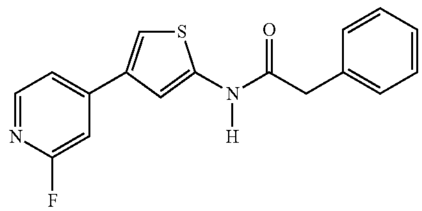 |
| 67 | 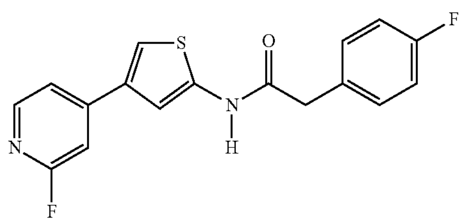 |
| 68 | 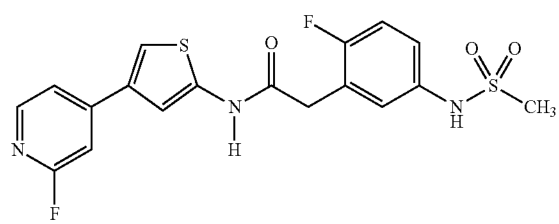 |
| 69 | 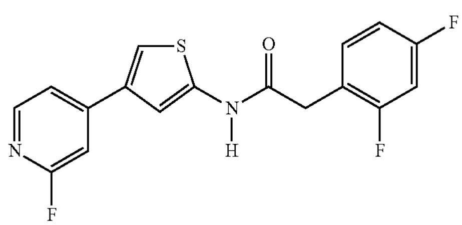 |
| 70 | 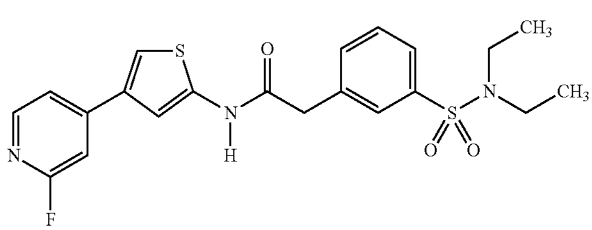 |
| 71 | 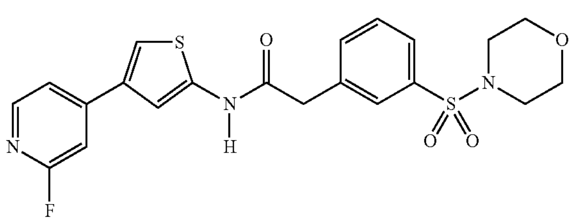 |

TABLE 1-continued

| Compound No. | Structure |
| --- | --- |
| 72 | 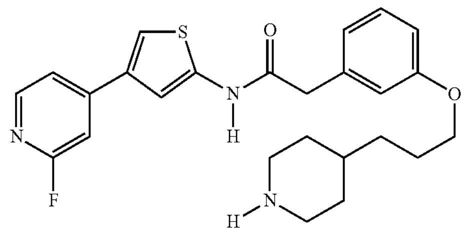 |
| 73 | 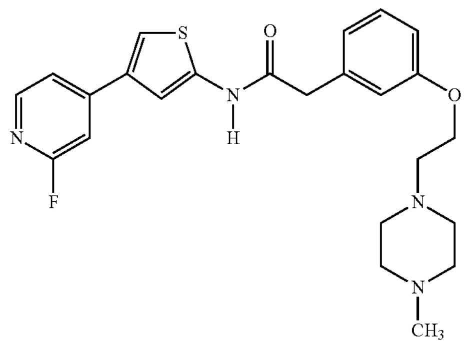 |
| 74 | 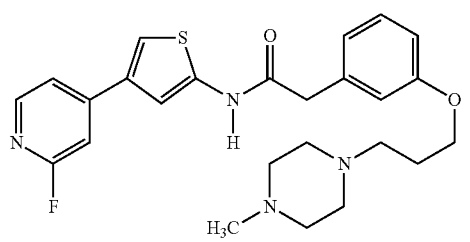 |
| 75 | 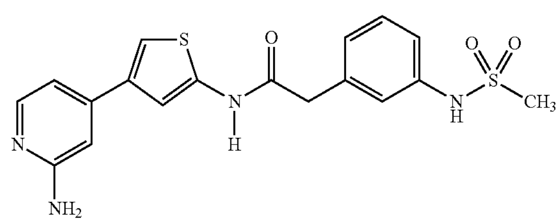 |
| 76 | 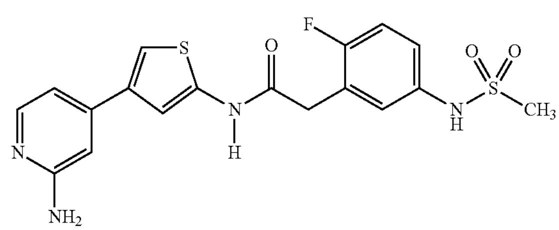 |
| 77 | 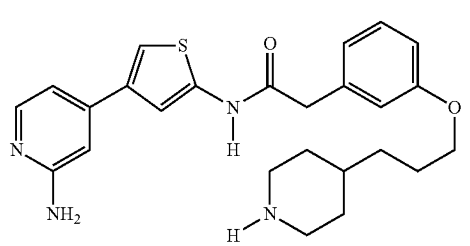 |

TABLE 1-continued

| Compound No. | Structure |
|---|---|
| 78 | 2-(3-(N,N-dimethylsulfamoyl)phenyl)-N-(4-(2-fluoropyridin-4-yl)thiophen-2-yl)acetamide |
| 79 | N-(4-(2-aminopyridin-4-yl)thiophen-2-yl)-2-(3-(N,N-dimethylsulfamoyl)phenyl)acetamide |
| 80 | 2-(3-methoxyphenyl)-N-(4-(2-methylpyridin-4-yl)thiophen-2-yl)acetamide |
| 81 | 2-(2-fluorophenyl)-N-(4-(2-methylpyridin-4-yl)thiophen-2-yl)acetamide |
| 82 | 2-(3-(methylsulfonamido)phenyl)-N-(4-(2-methylpyridin-4-yl)thiophen-2-yl)acetamide |
| 83 | 2-(3-(N,N-dimethylsulfamoyl)phenyl)-N-(4-(2-methylpyridin-4-yl)thiophen-2-yl)acetamide |
| 84 | 2-(3-(3,3-dimethylsulfamide)phenyl)-N-(4-(2-methylpyridin-4-yl)thiophen-2-yl)acetamide |

TABLE 1-continued

| Compound No. | Structure |
|---|---|
| 85 | 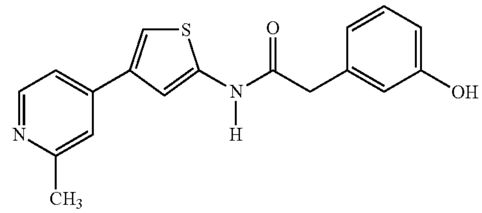 |
| 86 | 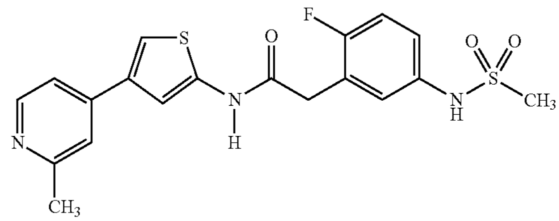 |
| 87 | 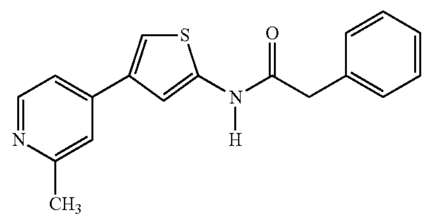 |
| 88 | 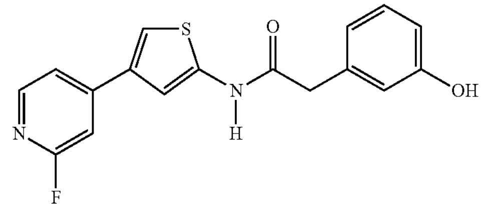 |
| 89 | 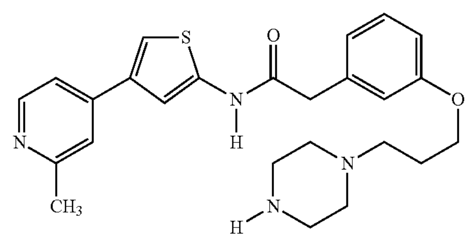 |
| 90 | 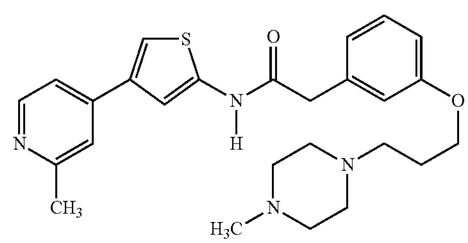 |
| 91 | 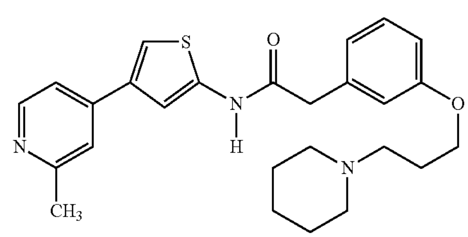 |

TABLE 1-continued
| Compound No. | Structure |
|---|---|
| 92 | 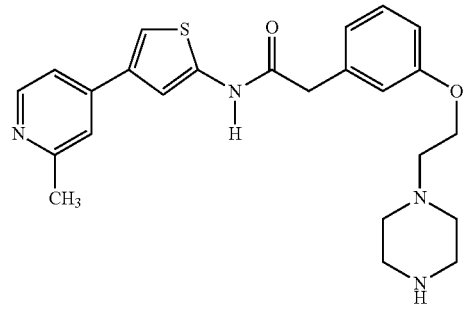 |
| 93 | 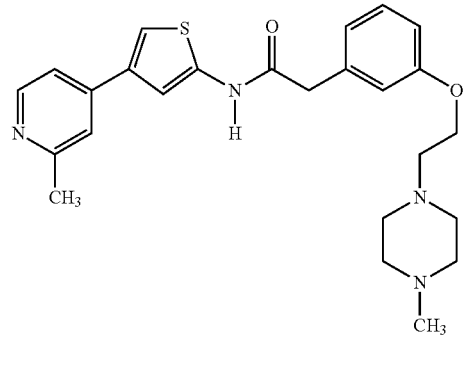 |
| 94 | 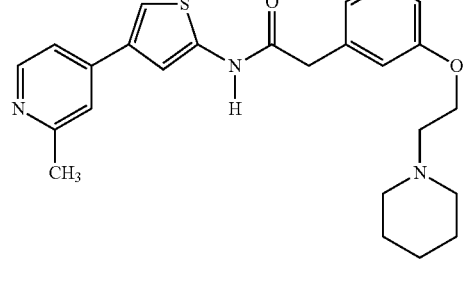 |
| 95 | 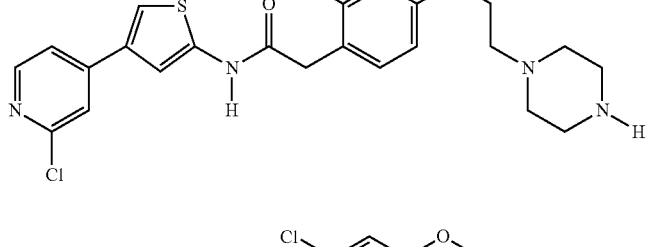 |
| 96 | 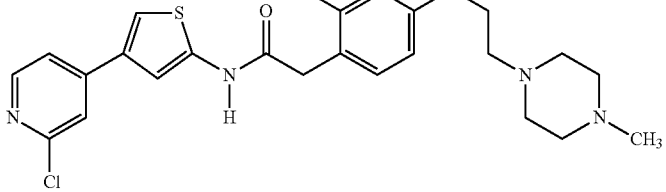 |

TABLE 1-continued

| Compound No. | Structure |
|---|---|
| 97 | (structure) |
| 98 | (structure) |
| 99 | (structure) |
| 100 | (structure) |
| 101 | (structure) |
| 102 | (structure) |

TABLE 1-continued

| Compound No. | Structure |
| --- | --- |
| 103 | 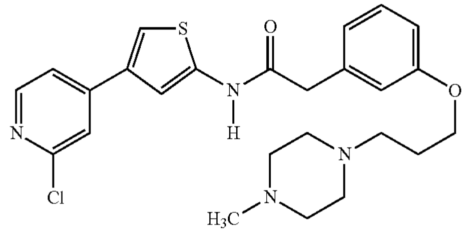 |
| 104 | 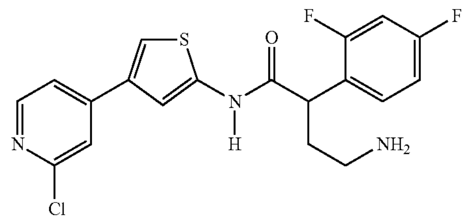 |
| 105 | 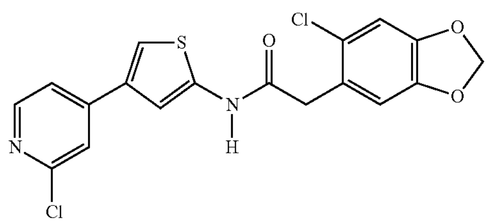 |
| 106 | 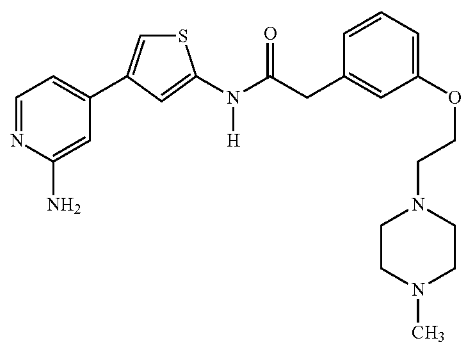 |
| 107 | 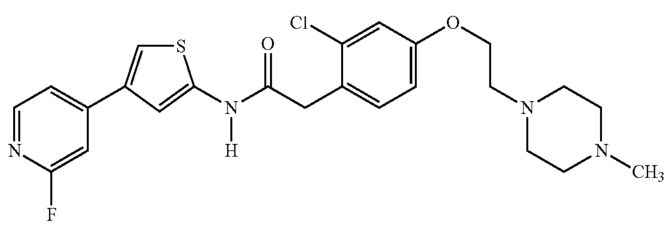 |

Formulation, Uses, and Administration

The compounds and compositions described herein are generally useful for the inhibition of protein kinase activity of one or more enzymes. In one particular embodiment, the compounds and compositions of the invention are inhibitors of ROCK and thus the compounds and compositions are particularly useful for treating or lessening the severity of disease or disease symptoms associated with ROCK.

The activity of a compound utilized in this invention as an inhibitor of ROCK may be assayed in vitro, in vivo or in a cell line. In vitro assays include assays that determine inhibition of either the phosphorylation activity or ATPase activity of activated ROCK. Alternate in vitro assays quantitate the ability of the inhibitor to bind to ROCK. Inhibitor binding may be measured by radiolabeling the inhibitor prior to binding, isolating the inhibitor/ROCK complex and determining the amount of radiolabel bound. Alternatively, inhibitor binding may be determined by running a competition experiment where new inhibitors are incubated with ROCK bound to known radioligands. Detailed conditions for assaying a compound utilized in this invention as an inhibitor of ROCK kinase are set forth in the Examples below.

In one embodiment, a compound of formula I or formula IA binds to ROCK with a $K_i$ of less than or equal to 0.1 micromolar as measured in vitro and inhibits at least one cytochrome P450 isozyme (such as, for example, CYP1A2, CYP2C19, CYP2C9, CYP2D6, or CYP3A4) with an $IC_{50}$ of greater than or equal to 5 micromolar as measured in vitro. In other embodiments, a compound of formula I or formula IA binds to ROCK with a $K_i$ of less than or equal to 0.1 micromolar and inhibits 3, 4, or all of the cytochrome P450 isozymes selected from the group consisting of CYP1A2, CYP2C19, CYP2C9, CYP2D6, and CYP3A4 with an $IC_{50}$ of greater than or equal to 10 micromolar.

According to another aspect, the invention features a composition comprising a compound of this invention or a pharmaceutically acceptable salt or prodrug thereof, and a pharmaceutically acceptable carrier, adjuvant, or vehicle. The amount of compound in the compositions of this invention is such that is effective to detectably inhibit a protein kinase, particularly ROCK, in a biological sample or in a patient. Preferably the composition of this invention is formulated for administration to a patient in need of such composition. Most preferably, the composition of this invention is formulated for oral administration to a patient.

The term "patient," as used herein, means an animal, preferably a mammal, and most preferably a human.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit," as used herein, means a measurable change in ROCK activity between a sample comprising a compound or composition of the invention and a ROCK kinase and an equivalent sample comprising ROCK kinase in the absence of the compound or composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ROCK.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral," as used herein, includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

According to another aspect, the invention features a method of inhibiting protein kinase activity, such as, for example, ROCK kinase activity, in a biological sample comprising the step of contacting the biological sample with a compound of this invention, or a composition comprising the compound.

The term "biological sample," as used herein, means a sample outside an animal and includes, without limitation, cell cultures or extracts thereof; biopsied material obtained from an animal or extracts thereof; and blood, saliva, urine, feces, semen, tears, or other body fluids or extracts thereof. Inhibition of kinase activity, particularly ROCK kinase activity, in a biological sample is useful for a variety of purposes known to one of skill in the art. Examples of such purposes include, but are not limited to, biological specimen storage and biological assays.

In another aspect, the invention features a method of inhibiting protein kinase activity, such as, for example, ROCK kinase activity, in a patient comprising the step of administering to the patient a compound of the present invention, or a composition comprising the compound.

According to another embodiment, the invention provides a method for treating or lessening the severity of an ROCK-mediated disease or condition in a patient comprising the step of administering to the patient a composition according to the present invention.

The term "ROCK-mediated disease" or "condition," as used herein, means any disease or other deleterious condition in which ROCK is known to play a role. ROCK participates in a variety of important physiological functions in the vasculature, including smooth muscle contraction; cell proliferation, such as, for example, vascular smooth muscle cell proliferation; and cell adhesion and migration (see Hu & Lee, *Expert Opin. Ther. Targets* 9(4):715-36, 2005; Shimokawa & Takeshita, *Arterioscler. Thromb. Vasc. Biol.* 25(9):1767-75, 2005). ROCK is participates in inflammatory responses due to leukocyte migration, such as, for example, autoimmune disease and allergic reactions (see Wettschureck et al., *J. Mol. Med.* 80:629-38, 2002). Abnormal activation of the Rho/ROCK pathway has been observed in various disorders of the central nervous system (see Mueller et al, *Nature Rev.* 4:387-98, 2005). In addition, ROCK has been implicated in tumor cell migration and invasion (Riento & Ridley, *Nature Rev.* 4:446-56, 2004) and in osteoporosis (Ohnaka et al., *Biochem. Biophys. Res. Commun.* 287(2):337-4, 2001).

Accordingly, another embodiment of the present invention relates to treating or lessening the severity of a disease or disorder in which ROCK is known to play a role. Specifically, the present invention relates to a method of treating or lessening the severity of a cardiovascular disease or disorder, such as, for example, cerebral vasospasm, hypertension, atherosclerosis, angina, myocardial infarction, ischemic/reperfusion injury, stroke, bronchial asthma; glaucoma, pre-term labor, erectile dysfunction, or renal disease, such as, for example, chronic renal failure, chronic nephritis, diabetic nephropathy, and IgA nephropathia; a neurological disease or disorder, such as for example, spinal-cord injury, Alzheimer's disease, multiple sclerosis, or neuropathic pain; and proliferative disorders, such as, for example, retinopathy, fibrosis, or invasive/metastatic cancers. Such cancers include adenocarcinoma, adrenocortical cancer; bladder cancer; bone cancer; brain cancer; breast cancer; cancer of the buccal cavity; cervical cancer; colon cancer; colorectal cancer; endometrial or uterine carcinoma; epidermoid carcinoma; esophogeal cancer; eye cancer; follicular carcinoma; gallbladder cancer; gastrointestinal cancer; cancer of the genitourinary tract; glioblastoma; hairy cell carcinoma; head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, small-cell lung cancer, squamous carcinoma of the lung, non-small cell lung cancer; melanoma; myeloproliferative disorders, neuroblastoma; ovarian cancer; papillary carcinoma; pancreatic cancer; cancer of the peritoneum; prostate cancer; rectal cancer; salivary gland carcinoma; sarcoma; squamous cell cancer; small cell carcinoma; cancer of the small intestine; stomach cancer; testicular cancer; thyroid cancer; and vulval cancer. In particular embodiments, the treated cancer is melanoma, breast cancer, colon cancer, or pancreatic cancer.

The treatment method that includes administering an ROCK inhibitor of the invention can further include administering to the patient an additional therapeutic agent (combination therapy) selected from: a chemotherapeutic or antiproliferative agent, an anti-inflammatory agent, an immunomodulatory or immunosuppressive agent, a neurotrophic factor, an agent for treating cardiovascular disease, an agent for treating destructive bone disorders, an agent for treating renal disease, or an agent for treating blood disorders, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration in normally within 5 hours or each other but may be staggered by, for example, 6 hours, 12 hours, 1 day, 2 days, 3 days, 1 week, 2 weeks, 3 weeks, 1 month, or 2 months. Non-limiting examples of chemotherapeutic agents or other anti-proliferative agents that may be combined with a compound of this invention include adriamycin, gemcitabine, cyclophosphamide, dexamethasone, etoposide, fluorouracil, Gleevec™, interferons, platinum derivatives, such as carboplatin, topotecan, taxol, vinblastine, and vincristine. Non-limiting examples of immunomodulatory agents that may be combined with a compound of this invention include alpha-, beta-, and gamma-interferons, pegylated derivatized interferon-α compounds, ribaviron, and thymosin. Non-limiting examples of immunosuppressive agents that may be combined with a compound of this invention include cyclosporin, tacrolimus, rapamycin, mycophenolate mofetil, interferons, corticosteroids, cyclophosphamide, azathioprine, and sulfasalazine. Non-limiting examples of neurotrophic factors that may be combined with a compound of this invention include acetylcholinesterase inhibitors, MAO inhibitors, interferons, anti-convulsants, ion channel blockers, riluzole, and anti-Parkinsonian agents. Non-limiting examples of agents for treating cardiovascular disease that may be combined with a compound of this invention include beta-blockers, ACE inhibitors, diuretics, nitrates, calcium channel blockers, and statins. Non-limiting examples of agents for treating blood disorders that may be combined with a compound of this invention include corticosteroids, anti-leukemic agents, and growth factors.

The amount of compound of the invention or the amount of compound and additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions that include an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

Preparation of the Compounds of the Invention

The compounds of the present invention may be prepared according to methods known to one or ordinary skill in the art and by those described in U.S. Patent Application No. 20040122016, the entirety of which is hereby incorporated by reference. Although certain exemplary embodiments are depicted and described herein, it will be appreciated that compounds of the invention can be prepared as generally described herein using appropriate starting materials that are commercially available or obtained by methods generally available to one of ordinary skill in the art. In order that the invention described herein may be more fully understood, the following examples are set forth. It should be understood that these examples are for illustrative purposes only and are not to be construed as limiting this invention in any manner.

The following definitions describe terms and abbreviations used herein:
ATP adenosine triphosphate
Boc tert-butoxycarbamate
BtS(O)$_2$Me N-(1-methanesulfonyl)benzotriazole
DMF dimethylformamide
ESMS electrospray mass spectrometry
HEPES 4-(2-hydroxyethyl)-1-piperazineethanesulfonic acid
HPLC high performance liquid chromatography
LCMS liquid chromatography-mass spectrometry
Me methyl
MeOH methanol
NADH nicotinamide adenine dinucleotide hydride
Ph phenyl
tBu tertiary butyl
TFA trifluoacetic acid
THF tetrahydrofuran Scheme 1 shows a general synthetic route useful for preparing compounds of formula I of this invention.

Scheme 1

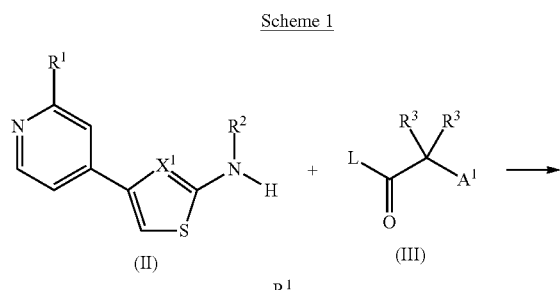

Accordingly, a compound of formula II, where $R^1$, $R^2$, and $X^1$ are as described herein, is reacted to a compound of formula III, where $R^3$ is as described herein and L is a leaving group. For example, L can be a halogen or an activated hydroxyl. Methods for activating hydroxyls are well known to those skilled in the art and include the use of conventional condensation reagents including, for example, 1-benzotriazol-1-yloxy-bis(pyrrolidino)uronium hexafluorophosphate (BBC), O-(7-azabenzotriazol-1-yl)-1,1,3,3-tetramethyluronium hexafluorophosphate (HATU), O-(7-azabenzotriazol-1-yl)-1,1,3,3-bis(tetramethylene)uronium hexafluorophosphate (HAPyU), O-(benzotriazol-1-yl)-1,1,3,3-tetramethyluronium hexafluorophosphate (HBTU), 1,3-diisopropylcarbodiimide (DIC), 1-ethyl-3-(3'-dimethylaminopropyl)carbodiimide hydrochloride, (EDCI) O-(7-azabenzotriazol-1-yl)-tris(dimethylamino)phosphonium hexafluorophosphate (AOP), 1-benzotriazolyoxytris (dimethylamino)phosphonium hexafluorophosphate (BOP), 7-azobenzotriazolyoxytris(pyrrolidino)phosphonium hexafluorophosphate (PyABOP), and 1-benzotriazolyoxytris (pyrrolidino)phosphonium hexafluorophosphate (PyBOP).

Synthetic procedures analogous to those used in the preparations of compounds of formulae IV, V, and VI, where $R^1$ is hydrogen, n is 1 to 3, and $TR^5$ is as defined herein, as well as their subsequent use to form compounds of formulae I and II, are found in U.S. Patent Application Publication No. 20040122016, which procedures are hereby incorporated by reference.

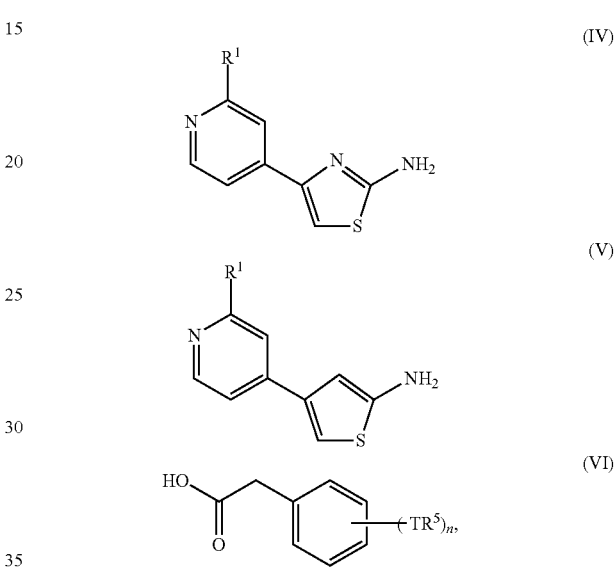

In another general example, thiazole-containing compounds of formula IX, where $R^1$ and $A^1$ are as defined herein, can be prepared as shown in Scheme 2, where a bromoacetyl compound of formula VII is reacted with a thiourea of formula VIII to produce a thiazole of formula IX.

Scheme 2

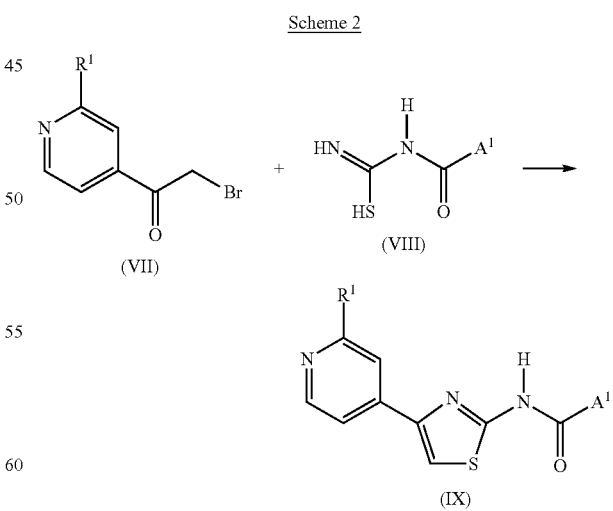

In yet another general example, thiophene-containing compounds of formula XIII, where $R^1$, n, and $TR^5$ are as defined herein, can be prepared as shown in Scheme 3. Accordingly, a boronic acid or boronic acid derivative of formula X is reacted with a thiophene of formula XI, where P is a suitable nitrogen protecting group (e.g., Boc), in a palladium catalyzed coupling reaction to form a compound of formula XII. The compound of formula XII is then coupled to an optionally substituted phenylacetic acid of formula VI to form a compound of formula XIII. In this example, the coupling is affected in the presence of N-(1-methanesulfonyl) benzotriazole (BtS(O)$_2$Me) by the application of microwave irradiation and heat.

Scheme 3

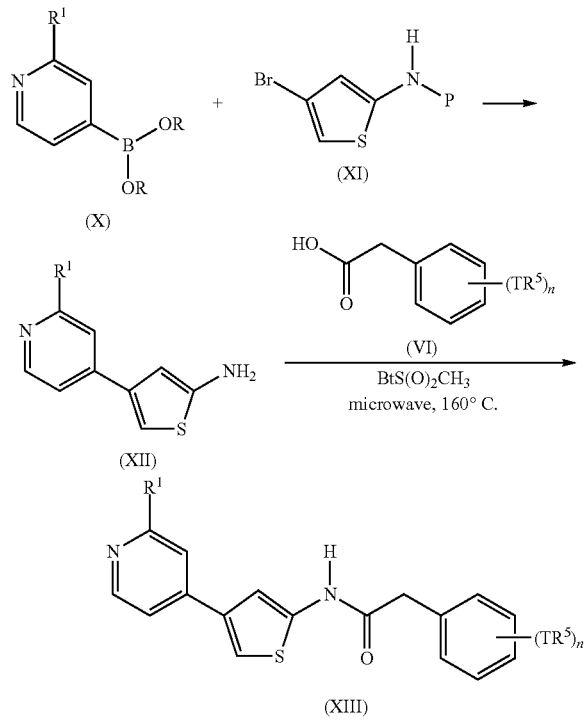

EXAMPLES

The following examples provide detailed methods for preparing exemplary compounds of the present invention. It will be appreciated that other compounds of the present invention are prepared in accordance with the teachings provided herein and with methods known to one or ordinary skill in the art.

Example 1

Preparation of Compound 18

Compound 18 was prepared as outlined in Scheme 4. Accordingly, potassium t-butoxide (6.1 g) was added slowly to a stirred solution of tert-butylnitrite (5.5 mL) and 2-fluoro-4-methylpyridine (compound 1001, 4.0 g) in 75 mL of THF at 0° C. After the addition was complete, the reaction mixture was stirred at room temperature for 2 hours. The reaction mixture was concentrated in vacuo and the crude product extracted with ethyl acetate (4×50 mL). The resulting solid was washed with hexanes to yield (2-fluoropyridin-4-yl) methan-N-hydroxyimine (compound 1002; 4.0 g; ESMS: M+H$^+$=141). Thionyl chloride (2.6 mL) was added slowly to a stirred solution of compound 1002 (4.0 g in 40 mL of THF) at 0° C. After stirring for 1 hour at room temperature, the volatiles were removed in vacuo. The residue was taken up in ethyl acetate (50 mL) and the organics were washed with water and brine. The organics were concentrated in vacuo to give 2-fluoropyridine-4-carbonitrile (compound 1003) as a white solid (3.0 g; ESMS: M+H$^+$=123). Compound 1003 (1.0 g) and 4-methoxybenzylamine were combined and heated at 130° C. for 1 hour. The crude product was partitioned between water and ethyl acetate (50 mL). The aqueous layer was extracted with ethyl acetate and the combined organics dried over Na$_2$SO$_4$, concentrated, and recrystallized from ethyl acetate/hexanes to provide 2-(4-methoxybenzylamino) pyridine-4-carbonitrile (compound 1004; 1.7 g; ESMS: M+H$^+$=238) as pale yellow solid. Compound 1004 (1.6 g) was dissolved in 50 mL of anhydrous ether and 9 mL of 3M methyl magnesium bromide in ether was added. The reaction mixture was stirred at room temperature for 16 hours and poured over ice (c. 50 g), which was subsequently acidified with 6M HCl, followed by basification with 1M ammonium hydroxide. The resulting mixture was extracted with ethyl acetate (3×50 mL). The combined organics were concentrated in vacuo and purified by silica gel chromatography to provide 1-(2-(4-methoxybenzylamino)pyridin-4-yl)ethanone (Compound 1005; 1.2 g; ESMS: M+H$^+$=257) as a yellow solid.

Separately, to 2-(3-methoxyphenyl)acetic acid (compound 1007, 1 g) in 25 mL of dichloromethane containing 0.1 mL of DMF was added 2.45 mL of 2M phosgene/CH$_2$Cl$_2$. The reaction mixture was stirred for 3 hours at room temperature and the volatiles were removed in vacuo. The residue was treated with 25 mL of THF and 1.82 g of thiourea, followed by heating at 80° C. for 3 hours. The mixture was cooled, poured into 20 mL of water, which was extracted with ethyl acetate (3×50 mL). The combined organics were concentrated and the residue recrystallized (ethyl acetate/hexanes) to provide 1-(2-(3-methoxyphenyl)acetyl)thiourea (compound 1008, 476 mg).

Compound 1005 (50 mg) was dissolved in 0.9 mL of acetic acid containing 0.2 mL of 48% HBr. Bromine (10 μL) was added and the reaction mixture was heated at 70° C. for 2 hours to produce intermediate compound 1006 (bromination of the acetyl group was accompanied by loss of the 4-methoxybenzyl protecting group), which was not isolated. Compound 1008 (44 mg in 7 mL of ethanol) was added and the reaction mixture heated at 70° C. for 1 hour. The reaction mixture was cooled, poured into 10 mL of water and the solution made basic with concentrated ammonium hydroxide. The mixture was concentrated in vacuo and the residue purified by reversed-phase HPLC (10-90% acetonitrile/water gradient containing 0.1% TFA) to provide N-(4-(2-aminopyridin-4-yl)thiazol-2-yl)-2-(3-methoxyphenyl)acetamide (compound 18, 36 mg; ESMS: M+H$^+$=341).

Scheme 4

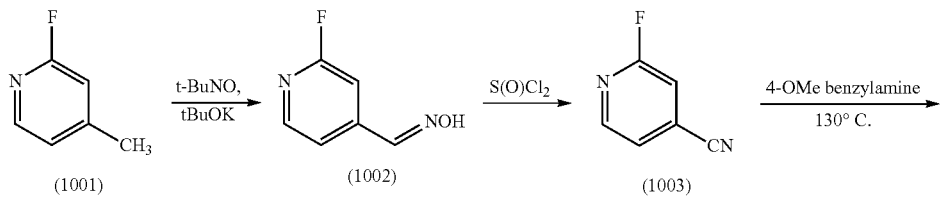

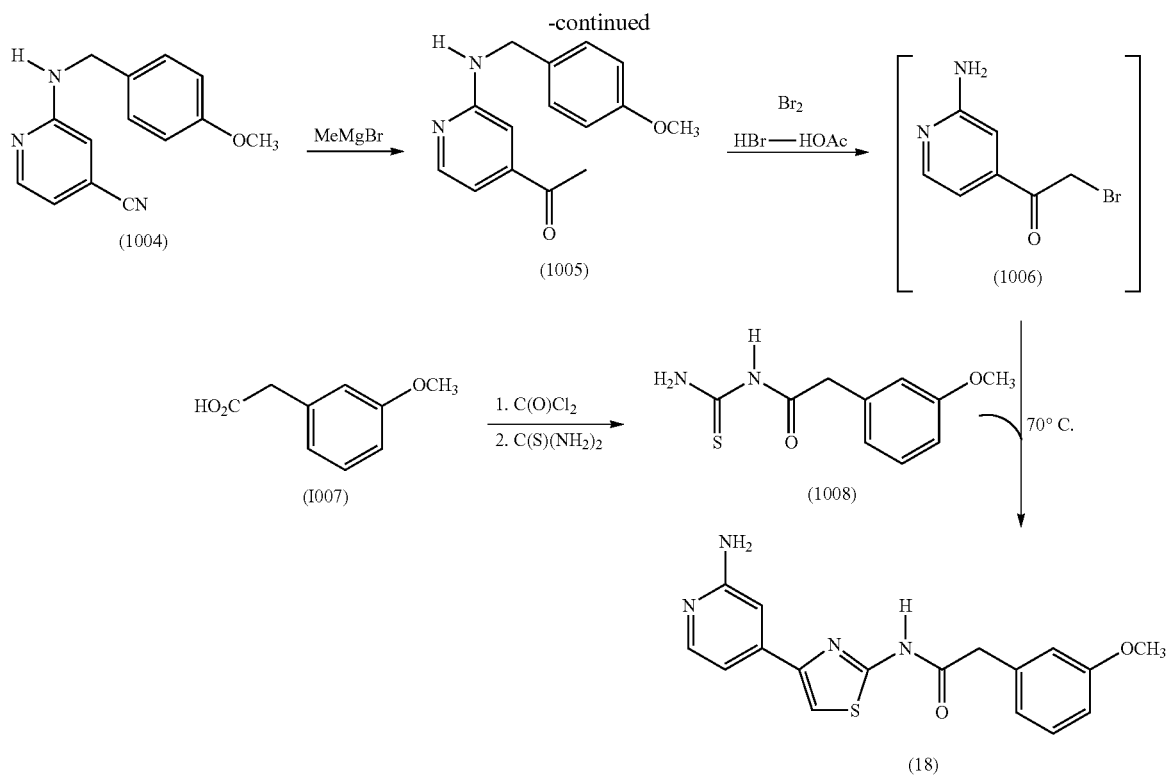

Example 2

Preparation of Compound 62

As shown in Scheme 5, a mixture of 4-bromothiophene-2-carboxylic acid (53 g, 255 mmol), diphenylphosphoryl azide (70 mL, 323 mmol), and triethylamine (45 mmol) in tertiary butanol (675 mL) was heated at 100° C. for 5 hours. After cooling to room temperature, the volatiles were removed in vacuo to give a brown gum, which was dissolved in ethyl acetate (500 mL). The organics were washed with saturated NaHCO$_3$ and water, followed by drying over Na$_2$SO$_3$ and concentration in vacuo. The residue was dissolved in a minimum amount of CH$_2$Cl$_2$ and purified by chromatography on silica gel (10-15% EtOAc/hexanes) to produce tert-butyl 4-bromothiophen-2-ylcarbamate as a white solid (compound 1010, 47 g, ESMS: M+H$^+$=2781). Compound 1010 (96.7 mg, 0.35 mmol) was treated with 2-chloro-4-(4,4,5,5-tetramethyl-1,3,2-dioxaborolan-2-yl)pyridine (compound 1011, obtained from 2-chloro-4-bromopyridine by lithiation and subsequent reaction with 2-chloro-4,4,5,5-tetramethyl-1,3,2-dioxaborolane), a catalytic amount of tetrakis(triphenylphosphine)palladium(0), and potassium carbonate (2.06 mmol, 284 mg) in dioxane/water (2.4 mL/0.8 mL) to produce tert-butyl 4-(2-chloropyridin-4-yl)thiazol-2-ylcarbamate (compound 1012, ESMS: M+H$^+$=311.5). The reaction mixture was dissolved in ethyl acetate, (10 mL) and washed with NaHCO$_3$ and H$_2$O. After drying, the solvent was removed in vacuo and the mixture carried forward without further purification. Compound 1012 was treated with 4M HCl/dioxane (3 mL) at room temperature for 2 hours. The resulting precipitate was filtered to produce 4-(2-chloropyridin-4-yl)thiazol-2-amine HCl salt (compound 1013, ESMS: M+H$^+$=211.5, 85% yield). Compound 1013 (30 mg, 0.14 mmol) was combined with 2-(3-methoxyphenyl)acetic acid (28 mg, 0.17 mmol), N-(1-methanesulfonyl)benzotriazole (55 mg, 0.28 mmol) and triethylamine (41 µL, 0.30 mmol) in 2 mL THF and the mixture irradiated with microwave radiation for 10 minutes at 160° C. After removal of the solvent, the reaction mixture was taken into ethyl acetate, washed with 2N NaOH, and water. After removal of the solvent, the reaction mixture was purified by reversed-phase HPLC to produced N-(4-(2-chloropyridin-4-yl)thiazol-2-yl)-2-(3-methoxyphenyl)acetamide (compound 62, ESMS: M+H$^+$=359, 33% yield).

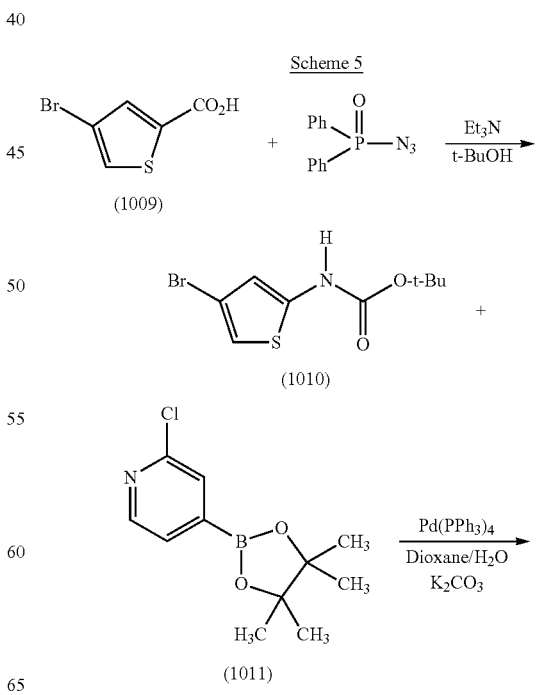

Scheme 5

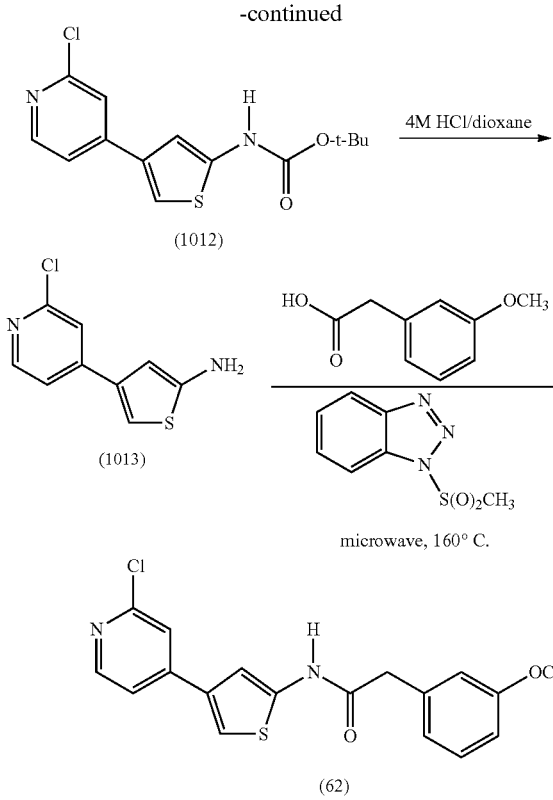

Example 3

Preparation of Compound 64

As shown in Scheme 6, 2.5 M n-BuLi (7.2 mL, 18 mmol) was added dropwise to a stirred solution of tert-butyl 4-bromothiophen-2-ylcarbamate (compound 1009, 1.0 g, 3.6 mmol) in 3 mL of THF and 11 mL of toluene at −78° C. The mixture was stirred at −78° C. for 1 hour and triisopropyl borate (2.0 mL, 9 mmol) was added. Stirring was continued at −78° C. for 30 minutes, followed by stirring at room temperature for 30 minutes. Ethyl acetate (50 mL) and 2M HCl (15 mL) were added to the reaction mixture and stirring was continued for 25 minutes. The organic layer was separated and the aqueous layer was extracted with ethyl acetate (2×25 mL). The combined organics were dried and concentrated in vacuo to provide 5-(tert-butoxycarbamyl)thiphen-3-yl-3-boronic acid as an oil (compound 1015, 0.8 g, ESMS: M+H$^+$=242), which was used in the next step as is without any subsequent purification. Compound 1015 was dissolved in 4M HCl/dioxane (10 mL) and methanol (2 mL) and the reaction mixture stirred at room temperature for 2 hours. The volatiles were removed in vacuo to provide 5-aminothiophen-3-yl-3-boronic acid (compound 1016, 0.58 g, ESMS: M+H$^+$=143) as a brown gum. This intermediate was used as is without any subsequent purification. Compound 1016 (50 mg, 0.34 mmol) and triethylamine (50 µl) in 3 mL of DMF at room temperature was treated with and 2-(3-methoxyphenyl)acetyl chloride (0.408 mmol). The reaction mixture was stirred at room temperature overnight. The reaction mixture was dissolved in ethyl acetate (2×5 mL) and extracted with 1N NaOH. The basic extracts were acidified with 6N HCl, extracted with EtOAc (2×5 mL), and washed with water and brine. After drying over Na$_2$SO$_4$, the solvent was evaporated in vacuo to provide 5-(2-(3-methoxyphenyl)acetamido)thiophen-3-yl-3-boronic acid (compound 1017, ESMS: M+H$^+$=292). Compound 1017 (from previous step) and tert-butyl 4-chloropyridin-2-ylcarbamate (compound 1018, 0.34 mmol) were dissolved in dioxane/water (3 mL/1 mL) under an atmosphere of nitrogen in microwave tube. A catalytic amount of trisdibenzylideneacetone palladium(0) was added, followed by the addition of three equivalents of potassium fluoride (and tri(tert-butyl)phosphine (0.045 mole %). The reaction mixture was heated under microwave irradiation at 180° C. for 15 min. After cooling, the organic layer was concentrated and the crude product dissolved in DMF and water, followed by reversed-phase HPLC purification to provide N-(4-(2-aminopyridin-4-yl)thiophen-2-yl)-2-(3-methoxyphenyl)acetamide (compound 67, 10 mg, 8.6% yield from 1016), ESMS: M+H$^+$=340).

Scheme 6

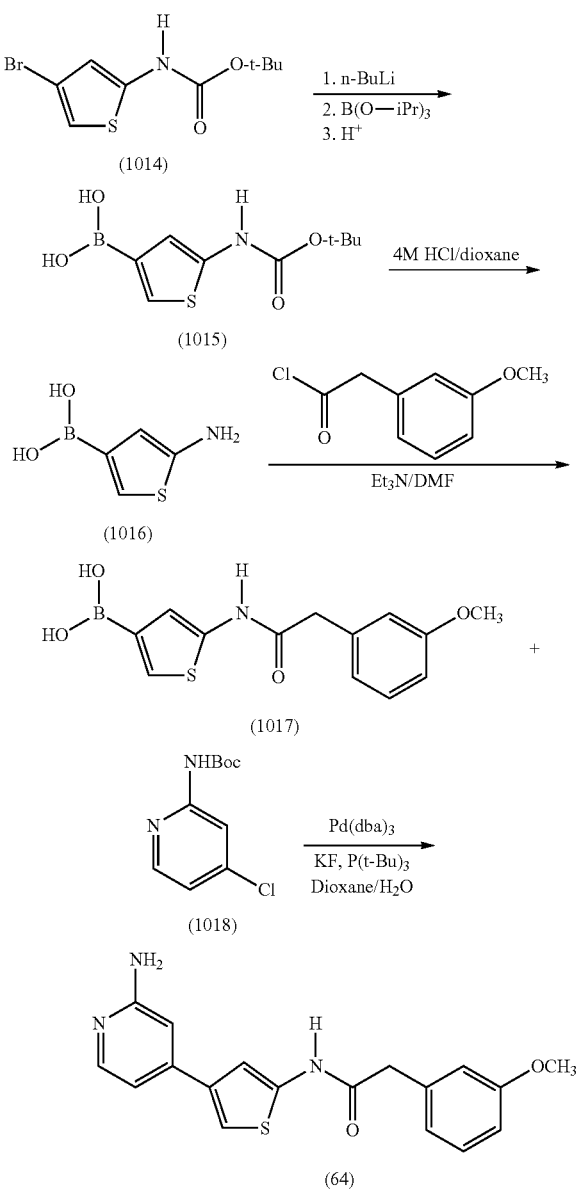

Spectral data for selected compounds of the invention are presented in Table 1.

TABLE 1

| Cmpd No. | $^1$H-NMR (500 MHz) NMR peaks given as δ values | ESMS (M + 1) |
|---|---|---|
| 1 | (DMSO-d$_6$): 12.57 (s, 1H), 8.45 (d, 1H), 8.11 (s, 1H), 7.94 (s, 1H), 7.85 (dd, 1H), 7.25 (t, 1H), 6.83-6.93 (m, 3H), 3.77 (s, 2H), 3.75 (s, 3H) | 360 |
| 2 | (methanol-d$_4$): 8.34 (d, 1H), 7.95 (s, 1H), 7.82-7.84 (m, 2H), 7.36 (m, 2H), 7.06 (m, 2H), 3.79 (s, 2H) | 348 |
| 3 | (DMSO-d$_6$): 12.53 (s, 1H), 8.20 (d, 1H), 7.95 (s, 1H), 7.45 (dd, 1H), 7.24 (m, 2H), 6.82-6.84 (m, 3H), 3.90 (s, 3H), 3.76 (s, 2H), 3.74 (s, 3H) | 356 |
| 4 | (CDCl$_3$): 12.50 (brs, 1H), 8.23 (d, 1H), 8.11 (s, 1H), 7.14-7.30 (m, 5H), 6.98 (t, 2H), 3.95 (s, 3H), 3.79 (s, 2H) | 344 |
| 5 | (methanol-d$_4$): 8.17 (d, 1H), 7.93 (s, 1H), 7.66 (dd, 1H), 7.58 (s, 1H), 7.24 (t, 1H), 6.92 (m, 2H), 6.83 (dd, 1H), 4.45 (q, 2H), 3.79 (s, 3H), 3.76 (s, 2H), 1.47 (t, 3H) | 370 |
| 6 | (DMSO-d$_6$): 12.52 (s, 1H), 8.18 (d, 1H), 7.94 (s, 1H), 7.43 (dd, 1H), 7.23 (s, 1H), 7.08 (s, 1H), 7.03 (s, 1H), 6.07 (s, 2H), 4.32 (q, 2H), 1.33 (t, 3H) | 418 |
| 7 | (methanol-d$_4$): 8.20 (d, 1H), 8.03 (s, 1H), 7.75 (dd, 1H), 7.69 (s, 1H), 7.37 (m, 2H), 7.06 (m, 2H), 4.49 (q, 2H), 3.80 (s, 2H), 1.50 (t, 3H) | 358 |
| 8 | (methanol-d$_4$): 8.21 (d, 1H), 8.05 (s, 1H), 7.77 (d, 1H), 7.72 (s, 1H), 7.41 (m, 2H), 7.30 (m, 2H), 4.51 (q, 2H), 4.01 (s, 2H), 1.51 (t, 3H) | 374 |
| 9 | (DMSO-d$_6$): 12.51 (s, 1H), 8.10 (d, 1H), 7.83 (s, 1H), 7.23 (d, 1H), 7.08 (s, 1H), 7.03 (d, 1H), 6.82-6.85 (m, 3H), 3.79 (s, 2H), 3.75 (s, 3H), 3.06 (s, 6H) | 369 |
| 10 | (DMSO-d$_6$): 12.7 (brs, 1H), 8.46 (d, 1H), 8.13 (s, 1H), 7.91 (s, 1H), 7.86 (d, 1H), 7.46 (m, 2H), 7.33 (m, 2H), 4.01 (s, 2H) | 364 |
| 11 | (methanol-d$_4$): 8.03 (d, 1H), 7.60 (s, 1H), 7.40 (m, 2H), 7.30 (m, 2H), 7.46 (m, 2H), 7.22 (s, 1H), 7.07 (s, 1H), 3.99 (s, 1H), 3.11 (s, 6H) | 373 |
| 12 | (methanol-d$_4$): 8.04 (s, 1H), 7.88 (d, 1H), 7.67 (s, 1H), 7.43 (d, 1H), 6.91 (s, 1H), 6.90 (s, 1H), 6.00 (s, 2H), 3.90 (s, 2H), 3.33 (s, 6H) | 417 |
| 13 | (DMSO-d$_6$): 12.58 (s, 1H), 8.28 (d, 1H), 8.10 (s, 1H), 7.80 (d, 1H), 7.56 (s, 1H), 7.23 (t, 1H), 6.83-6.93 (m, 3H), 3.77 (s, 2H), 3.75 (s, 3H) | 344 |
| 14 | (DMSO-d$_6$): 12.45 (s, 1H), 7.97 (d, 1H), 7.68 (s, 1H), 6.84-7.34 (m, 12H), 4.52 (d, 2H), 3.75 (s, 2H), 3.73 (s, 3H) | 431 |
| 15 | (DMSO-d$_6$): 12.47 (s, 1H), 7.97 (d, 1H), 7.69 (s, 1H), 7.24 (t, 1H), 6.82-6.93 (m, 5H), 6.48 (t, 1H), 3.75 (s, 2H), 3.74 (s, 3H), 3.27 (q, 2H), 1.16 (t, 3H) | 369 |
| 16 | (DMSO-d$_6$): 12.57 (s, 1H), 7.93 (d, 1H), 7.72 (s, 1H), 7.45 (m, 1H), 6.96-7.25 (m, 4H), 6.94 (s, 1H), 6.09 (brs, 2H), 3.87 (s, 2H), | 347 |
| 17 | (DMSO-d$_6$): 7.93 (d, 1H), 7.67 (s, 1H), 7.08 (s1H), 7.03 (s, 1H), 6.94 (d, 1H), 6.90 (s, 1H), 6.06 (s, 2H), 5.94 (s, 2H), 3.80 (s, 2H) | 389 |
| 20 | (DMSO-d$_6$): 12.49 (s, 1H), 7.99 (d, 1H), 7.71 (s, 1H), 7.24 (t, 1H), 6.82-6.94 (m, 5H), 6.48 (m, 1H), 3.75 (s, 2H), 3.74 (s, 3H), 2.79 (d, 3H) | 355 |
| 21 | (DMSO-d$_6$): 12.54 (s, 1H), 7.98 (d, 1H), 7.71 (s, 1H), 7.46 (m, 1H), 7.21 (m, 1H), 7.09 (m, 1H), 6.93 (d, 1H), 6.91 (s, 1H), 6.51 (t, 1H), 3.87 (s, 2H), 3.25 (q, 2H), 1.15 (t, 3H) | 375 |
| 22 | (DMSO-d$_6$): 12.47 (s, 1H), 7.98 (d, 1H), 7.69 (s, 1H), 7.08 (s, 1H), (7.03, m, 1H), 6.89-6.97 (m, 2H), 6.48 (t, 1H), 6.05 (s, 1H), 3.88 (s, 2H), 3.26 (q, 2H), 1.16 (t, 3H) | 417 |
| 23 | (DMSO-d$_6$): 12.56 (s, 1H), 7.99 (d, 1H), 7.73 (s, 1H), 7.45 (m, 1H), 7.24 (m, 1H), 7.09 (m, 1H), 6.95 (d, 1H), 6.90 (s, 1H), 6.50 (m, 1H), 3.87 (s, 2H), 2.79 (d, 3H), | 361 |
| 24 | (DMSO-d$_6$): 12.49 (s, 1H), 7.92 (d, 1H), 7.68 (s, 1H), 7.24 (t, 1H), 6.85-6.94 (m.5H), 5.95 (s, 2H), 4.08 (m, 2H), 3.75-3.82 (m, 2H), 2.16 (m, 2H) | 403 |
| 25 | (CDCl$_3$): 9.28 (brs, 1H), 8.09 (d, 1H), 7.20-7.33 (m, 7H), 6.79-6.93 (m, 5H), 4.51 (d, 2H), 3.61 (s, 2H), 3.75-3.82 (m, 2H), 2.16 (m, 2H) | 437 |
| 26 | (CDCl$_3$): 8.85 (brs, 1H), 8.08 (d, 1H), 7.20-7.34 (m, 6H), 6.79-6.92 (m, 5H), 5.99 (s, 2H), 4.52 (d, 2H), 3.66 (s, 2H) | 479 |
| 27 | (methanol-d$_4$): 7.90 (d, 1H), 7.56 (s, 1H), 7.39-7.43 (m, 2H), 7.29-7.31 (m, 2H), 7.09-7.11 (m, 2H), 3.99 (s, 1H) | 345 |
| 28 | (methanol-d$_4$): 7.91 (d, 1H), 7.62 (s, 1H), 7.39-7.41 (m, 2H), 7.29-7.31 (m, 2H), 7.09-7.12 (m, 2H), 3.99 (s, 1H), 2.92 (s, 3H) | 359 |

TABLE 1-continued

| Cmpd No. | $^1$H-NMR (500 MHz) NMR peaks given as δ values | ESMS (M + 1) |
|---|---|---|
| 29 | (methanol-d$_4$): 7.91 (d, 1H), 7.55 (s, 1H), 7.40 (m, 2H), 7.30 (m, 2H), 7.02-7.06 (m, 2H), 3.98 (s, 2H), 3.32 (m, 2H), 1.23 (t, 3H) | 373 |
| 30 | (CDCl$_3$): 9.31 (brs, 1H), 8.53 (d, 1H), 7.57 (s, 1H), 7.47 (d, 1H), 7.37 (s, 1H), 7.34 (m, 1H), 6.88-6.95 (m, 2H), 3.82 (s, 2H), 2.61 (s, 3H) | 346 |
| 31 | (CDCl$_3$): 9.15 (brs, 1H), 8.50 (d, 1H), 7.53 (s, 1H), 7.45 (dd, 1H), 7.33 (m, 2H), 6.91 (m, 1H), 6.86 (m, 1H), 3.83 (s, 3H), 3.80 (s, 2H), 2.59 (s, 3H) | 340 |
| 32 | (DMSO-d$_6$): 12.36 (brs, 1H), 8.47 (d, 1H), 7.91 (s, 1H), 7.71 (s, 1H), 7.62 (d, 1H), 7.08 (s, 1H), 7.04 (s, 1H), 6.07 (s, 2H), 3.88 (s, 2H), 2.50 (s, 3H) | 388 |
| 33 | (DMSO-d$_6$): 12.62 (s, 1H), 8.48 (d, 1H), 7.92 (s, 1H), 7.72 (s, 1H), 7.63 (d, 1H), 7.45 (m, 2H), 7.33 (m, 2H), 4.00 (s, 2H), 2.49 (s, 3H) | 344 |
| 34 | (methanol-d$_4$): 7.91 (s, 1H), 7.82 (d, 1H), 7.46 (s, 1H), 7.35 (dd, 1H), 7.14 (t, 1H), 6.81 (m, 2H), 6.70 (m, 1H), 3.73 (2s, 2H) | 327 |
| 35 | (DMSO-d$_6$): 12.55 (s, 1H), 7.93 (d, 1H), 7.69 (s, 1H), 7.16-7.41 (m, 4H), 6.91-6.95 (m, 2H), 5.94 (m, 2H), 3.80 (s, 2H) | 329 |
| 36 | (CDCl$_3$): 8.90 (s, 1H), 8.55 (d, 1H), 7.60 (s, 1H), 7.31-7.53 (m, 6H), 3.806 (s, 2H), 2.63 (s, 3H) | 310 |
| 37 | (DMSO-d$_6$): 9.36 (s, 1H), 8.47 (d, 1H), 7.91 (s, 1H), 7.71 (s, 1H), 7.62 (dd, 1H), 7.11 (m, 2H), 6.64-6.76 (m, 3H), 3.69 (s, 2H), 2.50 (s, 3H) | 326 |
| 38 | (DMSO-d$_6$): 12.61 (s, 1H), 8.48 (d, 1H), 7.92 (s, 1H), 7.72 (s, 1H), 7.64 (m, 1H), 7.32-7.42 (m, 2H), 7.17-7.21 (m, 2H), 3.90 (s, 2H), 2.50 (s, 3H) | 328 |
| 39 | (CDCl$_3$): 8.79 (brs, 1H), 8.49 (d, 1H), 7.52 (s, 1H), 7.43 (dd, 1H), 7.31 (m2H), 6.84-6.91 (m, 3H), 4.03 (t, 2H), 3.80 (s, 2H), 2.54 (s, 3H), 2.49-2.65 (brm, 8H), 2.27 (s, 3H), 1.96 (m, 2H) | 466 |
| 40 | (DMSO-d$_6$): 12.55 (s, 1H), 8.47 (d, 1H), 7.91 (s, 1H), 7.71 (s, 1H), 7.62 (dd, 1H), 7.36 (m, 2H), 7.15 (m, 2H), 3.80 (s, 2H), 2.50 (s, 3H) | 328 |
| 41 | (DMSO-d$_6$): 12.51 (s, 1H), 7.92 (d, 1H), 7.68 (s, 1H), 7.24-7.34 (m, 5H), 6.91-6.95 (m, 2H), 5.98 (brs, 2H), 3.80 (s, 2H) | 311 |
| 42 | (DMSO-d$_6$): 12.60 (s, 1H), 8.14 (s, 1H), 7.96 (d, 1H), 7.68 (s, 1H), 7.30-7.39 (m, 4H), 7.14-7.19 (m, 2H), 7.09 (s, 1H), 6.99 (s, 1H), 3.82 (s, 2H) | 329 |
| 43 | (methanol-d$_4$): 7.95 (s, 1H), 7.81 (d, 1H), 7.50 (d, 1H), 7.37 (dd, 1H), 7.13-7.33 (m, 4H), 3.81 (s, 2H), 2.96 (s, 3H) | 404 |
| 44 | (DMSO-d$_6$): 12.70 (brs, 1H), 9.80 (brs, 1H), 8.47 (d, 1H), 7.92 (s, 1H), 7.71 (s, 1H), 7.62 (d, 1H), 7.29 (t, 1H), 7.19 (s, 1H), 7.07-7.12 (m, 2H), 3.78 (s, 2H), 2.99 (s, 3H) | 403 |
| 45 | (methanol-d$_4$): 7.83 (d, 1H), 7.54 (s, 1H), 7.23 (t, 1H), 7.09 (m, 2H), 6.92 (m, 2H), 6.82 (m, 1H), 4.03 (t, 2H), 3.76 (s, 2H), 2.56 (brm, 10 H), 1.93-1.98 (m, 2H) | 467 |
| 46 | (DMSO-d$_6$): 12.64 (s, 1H), 8.46 (d, 1H), 8.13 (s, 1H), 7.94 (s, 1H), 7.86 (dd, 1H), 7.32-7.42 (m.2H), 7.17-7.21 (m, 2H), 3.90 (s, 2H) | 348 |
| 47 | (DMSO-d$_6$): 12.64 (s, 1H), 8.46 (d, 1H), 8.13 (s, 1H), 7.94 (s, 1H), 7.86 (dd, 1H), 7.46 (m, 1H), 7.24 (m, 1H), 7.08 (m, 1H), 3.89 (s, 2H) | 366 |
| 48 | (DMSO-d$_6$): 12.56 (s, 1H), 9.35 (s, 1H), 8.46 (d, 1H), 8.12 (s, 1H), 7.94 (s, 1H), 7.86 (dd, 1H), 7.11 (t, 1H), 6.74 (m, 2H), 6.65 (dd, 1H), 3.70 (s, 2H) | 346 |
| 49 | (DMSO-d$_6$): 12.60 (brs, 1H), 8.45 (d, 1H), 8.12 (s, 1H), 7.94 (s, 1H), 7.86 (dd, 1H), 7.08 (s, 1H), 7.04 (s, 1H), 6.07 (s, 2H), 3.89 (s, 2H) | 408 |
| 50 | (DMSO-d$_6$): 12.60 (s, 1H), 8.46 (d, 1H), 8.12 (s, 1H), 7.94 (s, 1H), 7.86 (dd, 1H), 7.25-7.34 (m, 5H), 3.81 (s, 2H) | 330 |
| 51 | (DMSO-d$_6$): 12.61 (s, 1H), 9.73 (s, 1H), 8.46 (d, 1H), 8.12 (s, 1H), 7.94 (s, 1H), 7.85 (dd, 1H), 7.29 (t, 1H), 7.19 (s, 1H), 7.10 (m, 2H), 3.79 (s, 2H), 2.99 (s, 3H) | 423 |
| 52 | (methanol-d$_4$): 7.89 (d, 2H), 7.74 (s, 1H), 7.23 (t, 1H), 7.07 (m, 2H), 6.81-6.92 (m, 3H), 4.02 (t, 2H), 3.75 (s, 2H), 2.84 (brm, 4H), 2.47-2.52 (brm, 6H), 1.95 (m, 2H) | 453 |
| 53 | (DMSO-d$_6$): 12.60 (brs, 1H), 8.45 (d, 1H), 8.12 (s, 1H), 7.94 (d, 1H), 7.86 (dd, 1H), 7.22 (t, 1H), 6.83-6.91 (m, 3H), 3.98 (t, 2H), 3.75 (s, 2H), 2.25-2.40 (brm, 10 H), 2.12 (s, 3H), 1.84 (m, 2H) | 486 |
| 54 | (DMSO-d$_6$): 12.65 (brs, 1H), 8.45 (d, 1H), 8.12 (s, 1H), 7.94 (s, 1H), 7.86 (dd, 1H), 7.22 (t, 1H), 6.81-6.91 (m, 3H), 3.98 (t, 2H), 3.76 (s, 2H), 2.20-2.45 (brm, 12 H), 1.86 (m, 2H), 0.95 (t, 3H) | 500 |

TABLE 1-continued

| Cmpd No. | ¹H-NMR (500 MHz) NMR peaks given as δ values | ESMS (M + 1) |
|---|---|---|
| 55 | (DMSO-$d_6$): 8.45 (d, 1H), 8.11 (s, 1H), 7.93 (s, 1H), 7.85 (dd, 1H), 7.22 (t, 1H), 6.81-6.91 (m, 3H), 3.98 (t, 2H), 3.75 (s, 2H), 3.29 (brs, 1H), 2.67 (m, 4H), 2.37 (m, 2H), 2.27 (brm, 4H), 1.84 (m, 2H) | 472 |
| 56 | (DMSO-$d_6$): 12.65 (s, 1H), 8.30 (d, 1H), 8.11 (s, 1H), 7.81 (d, 1H), 7.57 (s, 1H), 7.32-7.42 (m, 2H), 7.17-7.21 (m, 2H), 3.90 (s, 2H) | 332 |
| 57 | (DMSO-$d_6$): 12.59 (s, 1H), 8.28 (d, 1H), 8.12 (s, 1H), 7.80 (d, 1H), 7.56 (s, 1H), 7.38 (m, 2H), 7.16 (t, 2H), 3.81 (s, 2H) | 332 |
| 58 | (DMSO-$d_6$): 12.65 (s, 1H), 8.20 (d, 1H), 8.11 (s, 1H), 7.82 (d, 1H), 7.57 (s, 1H), 7.45 (m, 1H), 7.23 (m, 1H), 7.07 (m, 1H), 3.89 (s, 2H) | 350 |
| 59 | (DMSO-$d_6$): 12.61 (s, 1H), 9.72 (s, 1H), 8.28 (d, 1H), 8.10 (s, 1H), 7.80 (m, 1H), 7.56 (s, 1H), 7.29 (t, 1H), 7.12 (s, 1H), 7.07-7.12 (m, 2H), 3.79 (s, 2 H), 2.99 (s, 3H) | 407 |
| 60 | (methanol-$d_4$): 8.18 (d, 1H), 7.80 (s, 1H), 7.77 (m, 1H), 7.54 (s, 1H) 7.23 (t, 1H), 6.93 (m, 2H), 6.82 (dd, 1H), 4.04 (t, 2H), 3.76 (s, 2H), 2.45-2.75 (brm, 10H), 2.31 (s, 3H), 1.94-2.00 (m, 2H) | 470 |
| 61 | (CDCl$_3$): 8.19 (d, 1H), 8.0 (s, 1H), 7.35 (m, 2H), 7.02 (s, 1H), 6.90 (m, 2H), 6.84 (d, 2H), 3.83 (s, 3H), 3.79 (s, 2H) | 342.9 |
| 62 | (CD$_3$CN): 9.50 (s, 1H), 8.34 (d, 1H), 7.60 (s, 1H), 7.52 (s, 1H), 7.41 (s, 1H), 7.29 (s, 1H), 7.06 (s, 1H), 6.95 (m, 2H), 6.85 (m, 1H), 3.8 (s, 3H), 3.70 (s, 2H) | 359 |
| 63 | (CD$_3$CN): 9.55 (s, 1H), 8.5 (d, 1H), 7.64 (s, 1H), 7.56 (s, 1H), 7.53 (d, 1H), 7.43 (s, 1H), 7.36 (t, 1H), 7.27 (s, 1H), 7.18 (m, 2H), 7.08 (s, 1H), 3.73 (s, 2H), 2.97 (s, 3H) | 422 |
| 64 | (CD$_3$CN): 9.63 (s, 1H), 7.73 (m, 1H), 7.50 (m, 1H), 7.29 (m, 1H) 7.06 (m, 3H), 6.94 (m, 2H), 6.87 (m, 1H), 3.81 (s, 3H), 3.71 (s, 2H) | 340 |
| 65 | (CD$_3$CN): 9.60 (s, 1H), 8.20 (d, 1H), 7.60 (s, 1H), 7.50 (d, 1H), 7.45 (s, 1H), 7.37 (m, 1H), 7.28 (s, 1H), 7.22 (s, 1H), 7.18 (m, 2H), 7.10 (s, 1H), 3.69 (s, 2H), 2.98 (s, 3H) | 406 |
| 66 | (methanol-$d_4$): 8.14 (d, 1H), 7.54 (m, 2H), 7.34 (m, 3H), 7.25 (m, 1H), 7.13 (s, 1H), 3.74 (s, 2H) | 313 |
| 68 | (DMSO-$d_6$): 11.61 (s, 1H), 9.67 (s, 1H), 8.23 (d, 1H), 7.74 (d, 1H), 7.60 (d, 1H), 7.43 (s, 1H), 7.14-7.24 (m, 4H), 3.78 (s, 2H), 2.93 (s, 3H) | 424 |
| 69 | (DMSO-$d_6$): 8.23 (d, 1H), 7.74 (d, 1H), 7.61 (m, 1H), 7.44 (m, 2H), 7.20 (m, 1H), 7.14 (d, 1H), 7.07 (m, 1H), 3.78 (s, 2H) | 349 |
| 70 | (methanol-$d_4$): 8.15 (d, 1H), 7.82 (d, 1H), 7.72 (dd, 1H), 7.61 (dd, 1H), 7.71-7.56 (m, 3H), 7.26 (d, 1H), 7.14 (d, 1H), 7.14 (d, 1H), 3.83 (s, 2H), 3.22 (q, 4H), 1.09 (t, 6H) | 448 |
| 71 | (methanol-$d_4$): 8.15 (d, 1H), 7.78 (d, 1H), 7.69 (m, 2H), 7.63 (m, 1H), 7.55 (m, 2H), 7.28 (d, 1H), 7.15 (d, 1H), 3.87 (s, 1H), 3.68 (m, 4H), 2.97 (m, 4H) | 462 |
| 72 | (methanol-$d_4$): 8.1 (d, 1H), 7.54 (m, 2H), 7.27 (s, 1H), 7.23 (t, 1H), 7.14 (d, 1H), 6.91 (m, 2H), 6.82 (m, 1H), 3.99 (t, 2H), 3.69 (s, 2H), 3.35 (m, 2H), 2.95 (m, 2H), 1.98 (m, 2H), 1.80 (m, 2H), 1.65 (brm, 1H), 1.48 (m, 2H), 1.37 (m, 2H) | 454 |
| 73 | (methanol-$d_4$): 8.14 (d, 1H), 7.52 (m, 2H), 7.22-7.26 (m, 2H), 7.13 (d, 1H), 6.93 (m, 2H), 6.84 (dd, 1H), 4.13 (t, 2H), 3.69 (s, 1H), 2.80 (t, 2H), 2.40-2.60 (brm, 8H), 2.26 (s, 3H) | 455 |
| 74 | (methanol-$d_4$): 8.15 (d, 1H), 7.52 (m, 2H), 7.23-7.27 (m, 2H), 7.14 (d, 1H) 6.92 (m, 2H), 6.84 (dd, 1H), 4.11 (t, 2H), 3.70 (s, 1H), 3.30-3.55 (brm, 8H), 3.20 (m, 2H), 2.91 (s, 3H), 2.16 (m, 2H) | 469 |
| 75 | (DMSO-$d_6$): 11.4 (brs, 1H), 7.87 (d, 1H), 7.30 (s, 1H), 6.92 (m, 2H), 6.72-6.80 (m, 3H), 6.61 (s, 1H), 6.49 (d, 1H), 5.86 (s, 2H), 3.48 (s, 2H), 2.57 (s, 3H) | 403 |
| 76 | (DMSO-$d_6$): 11.49 (brs, 1H), 9.70 (brs, 1H), 7.89 (d, 1H), 7.35 (s, 1H), 7.13-7.34 (m, 3H), 6.97 (d, 1H), 6.73 (dd, 1H), 6.61 (s, 1H), 5.88 (s, 2H), 3.74 (s, 2H), 2.94 (s, 3H) | 421 |
| 77 | (methanol-$d_4$): 7.85 (d, 1H), 7.30 (d, 1H), 7.20 (t, 1H), 7.05 (d, 1H), 6.77-6.90 (m, 5H), 3.96 (t, 2H), 3.67 (s, 2H), 3.02 (brm, 2H), 2.57 (m, 2H), 1.71-1.79 (m, 4H), 1.40 (m, 2H), 1.14 (m, 2H) | 451 |
| 78 | (methanol-$d_4$): 8.15 (d, 1H), 7.79 (s, 1H), 7.70 (d, 1H), 7.66 (t, 1H), 7.60 (t, 1H), 7.53 (m, 2H), 7.27 (s, 1H), 7.14 (s, 1H), 3.86 (s, 1H), 2.68 (s, 6H) | 420 |
| 79 | (methanol-$d_4$): 7.78 (m, 2H), 7.70 (m, 1H), 7.65 (m, 2H), 7.60 (m, 1H), 7.18 (d, 1H), 7.15 (d, 1H), 3.87 (s, 2H), 2.67 (s, 6H) | 417 |
| 80 | (methanol-$d_4$): 8.53 (d, 1H), 8.08 (s, 1H), 8.02 (d, 1H), 7.9 (s, 1H) 7.28 (s, 1H), 7.23 (m, 1H), 6.94 (m, 2H), 6.83 (d, 1H), 3.78 (s, 3H), 3.7 (s, 2H), 2.75 (s, 3H) | 338.9 |

TABLE 1-continued

| Cmpd No. | $^1$H-NMR (500 MHz) NMR peaks given as δ values | ESMS (M + 1) |
|---|---|---|
| 81 | (methanol-d$_4$): 8.56 (d, 1H), 8.08 (s, 1H), 7.99 (d, 1H), 7.87 (s, 1H), 7.47 (m, 1H), 7.38 (m, 2H), 7.15 (m, 2H), 3.83 (s, 2H), 2.75 (s, 3H) | 326.9 |
| 82 | (methanol-d$_4$): 8.53 (d, 1H), 8.08 (s, 1H), 8.00 (d, 1H), 7.9 (s, 1H), 7.28 (m, 3H), 7.12 (m, 2H), 3.75 (s, 2H), 2.95 (s, 3H), 2.75 (s, 3H) | 402 |
| 83 | (methanol-d$_4$): 8.53 (d, 1H), 8.08 (s, 1H), 8.02 (d, 1H), 7.9 (s, 1H), 7.78 (s, 1H), 7.67 (m, 2H), 7.59 (m, 1H), 7.30 (s, 1H), 3.88 (s, 2H), 2.78 (s, 3H), 2.67 (s, 6H) | 416 |
| 84 | (methanol-d$_4$): 8.53 (d, 1H), 8.10 (s, 1H), 8.02 (d, 1H), 7.92 (s, 1H), 7.26 (m, 3H), 7.12 (d, 1H), 7.05 (d, 1H), 3.73 (s, 2H), 2.77 (s, 3H), 2.72 (s, 6H) | 431 |
| 85 | (methanol-d$_4$): 8.53 (d, 1H), 8.05 (s, 1H), 7.98 (d, 1H), 7.88 (s, 1H), 7.27 (s, 1H), 7.12 (m, 1H), 6.77 (m, 2H), 6.68 (d, 1H), 3.65 (s, 2H), 2.75 (s, 3H) | 324.9 |
| 86 | (CD$_3$CN): 9.01 (s, 1H), 8.53 (d, 1H), 7.9 (s, 1H), 7.88 (d, 1H), 7.72 (s, 1H), 7.60 (s, 1H), 7.32 (m, 1H), 7.25 (m, 1H), 7.20 (s, 1H), 3.81 (s, 2H), 2.97 (s, 3H), 2.74 (s, 3H) | 420 |
| 87 | (CD$_3$CN): 9.76 (s, 1H), 8.56 (d, 1H), 7.85 (s, 1H), 7.82 (d, 1H), 7.64 (s, 1H), 7.34 (m, 3H), 7.27 (m, 2H), 7.15 (s, 1H), 3.73 (s, 2H), 2.73 (s, 3H) | 308.9 |
| 88 | (methanol-d$_4$): 8.15 (d, 1H), 7.56 (d, 2H), 7.29 (s, 1H), 7.15 (m, 2H), 6.8 (d, 2H), 6.69 (m, 1H), 3.63 (s, 2H) | 328.9 |
| 89 | (DMSO-d$_6$): 11.63 (s, 1H), 8.7 (bs, 1H), 8.66 (d, 1H), 7.93 (m, 3H), 7.24 (m, 2H), 6.92 (m, 2H), 6.85 (m, 1H), 4.0 (t, 2H), 3.68 (s, 2H), 3.22 (bs, 4H), 2.90 (bs, 4H), 2.65 (s, 3H), 2.1 (s, 2H), 2.0 (bs, 2H) | 450.95 |
| 90 | (DMSO-d$_6$): 11.63 (s, 1H), 8.70 (d, 1H), 8.10 (s, 1H), 8.0 (s, 2H), 7.25 (t, 2H), 6.92 (m, 2H), 6.85 (m, 1H), 4.0 (t, 2H), 3.70 (s, 2H), 3.22 (bs, 4H), 2.90 (bs, 4H), 2.77 (s, 3H), 2.70 (s, 3H), 2.1 (s, 2H), 2.0 (bs, 2H) | 464.9 |
| 91 | (DMSO-d$_6$): 11.67 (s, 1H), 9.05 (bs, 1H), 8.70 (d, 1H), 8.1 (s, 1H), 8.05 (m, 1H), 7.28 (m, 2H), 6.95 (m, 2H), 6.85 (d, 1H), 4.07 (t, 2H), 3.85 (s, 2H), 3.52 (d, 2H), 3.23 (m, 2H), 2.92 (m, 2H), 2.82 (s, 3H), 2.15 (m, 2H), 1.85 (m, 2H), 1.67 (m, 3H), 1.41 (m, 1H) | 550.0 |
| 92 | (DMSO-d$_6$): 11.63 s 91H), 8.69 (d, 1H), 8.60 (bs, 1H), 7.95 (m, 3H), 7.26 (m, 2H), 6.95 (d, 2H), 6.88 (d, 1H), 4.12 (t, 2H), 3.71 (d, 2H), 3.19 (bs, 4H), 2.92 (m, 4H), 2.69 (s, 3H), 2.11 (s, 2H) | 436.9 |
| 93 | (DMSO-d$_6$): 11.62 (s, 1H), 8.65 (d, 1H), 7.95 (m, 3H), 7.26 (m, 2H), 6.93 (d, 2H), 6.85 (d, 1H), 4.1 (bs, 2H), 3.7 (s, 2H), 3.38 (m, 2H), 3.15 (m, 2H), 3.0 (m, 1H), 2.85 (bs, 1H), 2.76 (bs, 2H), 2.66 (s, 3H), 2.07 (s, 2H) | 450.95 |
| 94 | (DMSO-d$_6$): 11.67 (s, 1H), 9.31 (bs, 1H), 8.7 (d, 1H), 8.1 (s, 1H), 8.0 (m, 2H), 7.3 (t, 1H), 7.24 (s, 1H), 6.96 (m, 2H), 6.9 (m, 1H), 4.32 (t, 2H), 3.85 (s, 2H), 3.52 (m, 4H), 3.03 (m, 2H), 2.72 (s, 3H), 1.83 (m, 2H), 1.70 (m, 3H), 1.4 (m, 1H), | 435.9 |
| 107 | (methanol-d$_4$): 7.86 (d, 1H), 7.34 (s, 1H), 7.25 (t, 1H), 7.07 (s, 1H), 6.94 (m, 2H), 6.86 (m, 2H), 6.80 s 91H), 4.16 (t, 2H), 3.70 (s, 2H), 2.88 (t, 2H), 2.73 (bs, 8H), 2.45 (s, 3H) | 452.1 |

Example 4

ROCK Inhibition Assay

Compounds were screened for their ability to inhibit ROCK I (AA 6-553) activity using a standard coupled enzyme system (Fox et al. *Protein Sci.* 7:2249, 1998). Reactions were carried out in a solution containing 100 mM HEPES (pH 7.5), 10 mM MgCl$_2$, 25 mM NaCl, 2 mM DTT and 1.5% DMSO. Final substrate concentrations in the assay were 45 μM ATP (Sigma Chemicals, St Louis, Mo.) and 200 μM peptide (American Peptide, Sunnyvale, Calif.). Reactions were carried out at 30° C. and 45 nM ROCK I. Final concentrations of the components of the coupled enzyme system were 2.5 mM phosphoenolpyruvate, 350 μM NADH, 30 ng/ml pyruvate kinase and 10 μg/ml lactate dehydrogenase. Results are shown in Table 2, where a K$_i$ of less than 0.1 μM is defined as "A," a K$_i$ of between 0.1 μM and 1.0 μM is defined as "B," and a K$_i$ of greater than 1.0 μM is defined as "C."

TABLE 2

| Compound No. | ROCK K$_i$ |
|---|---|
| 1 | B |
| 2 | B |
| 3 | C |
| 4 | C |
| 5 | C |
| 6 | C |
| 7 | C |
| 8 | C |
| 9 | C |
| 10 | B |
| 11 | C |
| 12 | C |
| 13 | B |
| 14 | C |
| 15 | B |
| 16 | A |
| 17 | A |

TABLE 2-continued

| Compound No. | ROCK $K_i$ |
|---|---|
| 20 | B |
| 21 | B |
| 22 | B |
| 23 | B |
| 24 | B |
| 25 | B |
| 26 | B |
| 27 | A |
| 28 | B |
| 29 | B |
| 30 | B |
| 31 | B |
| 32 | A |
| 33 | B |
| 34 | A |
| 35 | A |
| 36 | B |
| 37 | A |
| 38 | B |
| 39 | B |
| 40 | B |
| 41 | A |
| 42 | B |
| 43 | B |
| 44 | B |
| 45 | A |
| 46 | B |
| 47 | B |
| 48 | A |
| 49 | A |
| 50 | B |
| 51 | B |
| 52 | A |
| 53 | A |
| 54 | A |
| 55 | A |
| 56 | A |
| 57 | B |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | B |
| 72 | A |
| 73 | A |
| 74 | A |
| 75 | A |
| 76 | A |
| 77 | A |
| 78 | B |
| 79 | B |
| 80 | B |
| 81 | B |
| 82 | B |
| 83 | C |
| 84 | B |
| 85 | A |
| 86 | A |
| 87 | B |
| 88 | A |
| 89 | A |
| 90 | B |
| 91 | C |
| 92 | B |
| 93 | B |
| 94 | C |
| 95 | A |
| 96 | A |
| 97 | A |
| 98 | A |
| 99 | A |
| 100 | A |
| 101 | A |
| 102 | A |
| 103 | A |
| 104 | B |
| 105 | A |
| 106 | A |
| 107 | A |

Example 5

Cytochrome P450 Inhibition

Selected compounds of the invention were assayed for their ability to inhibit various cytochrome P450 isozymes, such as, for example CYP2D6, CYP2C9, CYP1A2, CYP2C19, CYP3A4, CYP2C9, and CYP3A4 (human liver microsome). Such assays are described by Crespi et al., *Anal. Biochem.* 248:188-90, 1997; Ekins et al., *J. Pharmacol. Exp. Ther.* 290, 429-38, 1999; and Ekins et al., *J. Pharmacol. Exp. Ther.* 291, 424-33, 1999. In a typical isozyme inhibition experiment, test compounds are placed into a microwell on a microtiter plate as an 8 nL solution (2 mM in 75% DMSO/water). The plate is centrifuged for 2 minutes at approximately 1000 rpm to shift the compound to the bottom of the well. Polyvinylpyrrolidone (PVP/10K, 100 nL, 0.2% in 75% DMSO/water) is added to the well and this excipient also centrifuged for 2 minutes at approximately 1000 rpm to ensure mixing with the compound. The plates containing the wells are dried in vacuo. Distilled water (800 nL) is added to the wells containing compound, the background control wells, and the positive control wells, followed by the addition of 200 nL of phosphate buffer (500 mM potassium phosphate butter at pH=8.4). The positive control cells contain a drug such as, for example, miconazole. Insect baculosomes (PanVera P2315) in 500 nM phosphate buffer was added to the background control wells and the plate was scanned for compound fluorescence. NADP$^+$ (200 nL, 100 µM) and substrate (3A4:5 µM Vivid™ 3A4 Red, 2C9:1 µM Vivid™ 2C9 Green, 1A2:2 µM Vivid™ 1A2 Blue, 2C19:10 µM Vivid™ 2C19 Blue, and 2D6:10 µM Vivid™ 2D6 Blue) in 100 mM phosphate buffer was added to each cell at a final concentration corresponding to the $K_m$ of the substrate for its pertinent CYP450 isozyme. Therefore, CYP450 isozyme (400 nL) and recycling buffer (3.3 mM glucose-6-phosphate, 0.4 units/mL glucose-6-phosphate dehydrogenase, 100 mM MgCl$_2$, and 0.00025% Antifoam 289) in 100 mM phosphate buffer was added to each well containing compound and background control to obtain the following concentrations: 5 nM CYP3A4, 10 nM CYP2C9, 5 nM CYP1A2, 5 nM CYP2C19, and 20 nM CYP2D6. After incubation for 60 minutes, the wells were read with a fluorescent plate reader. Cytochrome P450 isozyme inhibition values are given in Table 3, where an IC$_{50}$ of less than 1.0 µM is defined as "A," an IC$_{50}$ of between 1.0 µM and 10.0 µM is defined as "B," and an IC$_{50}$ of greater than 10.0 µM is defined as "C."

TABLE 3

| Compound No. | CYP1A2 $K_i$ | CYP2C19 $K_i$ | CYP2C9 $K_i$ | CYP2D6 $K_i$ | CYP3A4 $K_i$ | CYP3A4 (HLM) $K_i$ |
|---|---|---|---|---|---|---|
| 61 | C | B | B | C | B | B |
| 62 | C | — | B | — | B | B |
| 64 | B | C | B | B | B | C |
| 72 | C | B | — | B | B | C |
| 73 | C | — | C | C | C | C |
| 74 | C | C | C | C | C | C |
| 77 | C | B | B | A | B | B |
| 80 | C | B | B | C | B | B |
| 85 | C | B | C | C | C | C |
| 89 | C | B | C | — | C | C |
| 90 | C | — | C | — | C | C |
| 91 | C | C | C | — | C | C |
| 92 | C | C | C | — | C | C |
| 93 | C | C | C | — | C | C |
| 94 | C | C | C | — | C | C |
| 101 | B | B | B | — | B | B |
| 102 | C | B | C | C | B | C |
| 103 | C | C | C | C | C | C |
| 105 | B | A | B | A | B | B |
| 107 | C | C | C | A | — | C |

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

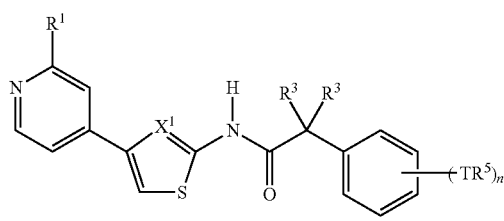

(I-A)

or a pharmaceutically acceptable salt thereof, wherein:
$R^1$ is halogen, —$NR_2$, —OR, —SR, or a $C_{1-4}$ alkyl;
$R^2$ is hydrogen or $C_{1-3}$ aliphatic;
each $R^3$ is, independently, hydrogen or a $C_{1-4}$ alkyl;
$X^1$ is N;
T is a bond or a $C_1$-$C_6$ alkylidene chain, wherein up to two methylene units of T are optionally and independently replaced by —NR'—, —S—, —O—, —C(O)NR'—, —NR'C(O)—, —NR'C(O)O—, —S(O)$_2$NR'—, —NR'S(O)$_2$—, —NR'C(O)NR'—, —OC(O)NR'—, or —NR'S(O)$_2$NR'—;
each $R^5$ is, independently, $R^a$ or halogen;
n is 1 to 3;
each occurrence of $R^a$ is, independently, hydrogen, an optionally substituted moiety selected from a $C_{1-4}$ alkyl group, a $C_{3-6}$ cycloalkyl group, a $C_{1-4}$ haloalkyl group, or a heterocyclic ring selected from morpholino, piperidinyl, or piperazinyl;

each optionally substituted group or ring is optionally substituted with 1-5 substituents independently selected from $C_{1-4}$ alkyl, $C_{3-6}$ cycloalkyl, $C_{1-4}$ haloalkyl, halogen, or —OR";
each occurrence of R is, independently, hydrogen, a $C_{1-4}$ alkyl group, a $C_{3-6}$ cycloalkyl group, —(CH$_2$)$_{1-2}$Ph, —CH=CHPh, or a $C_{1-4}$ haloalkyl group;
each occurrence of R' is, independently, hydrogen or a $C_{1-4}$ alkyl group; and
each occurrence of R" is, independently, hydrogen or a $C_{1-4}$ alkyl group.

2. The compound according to claim 1 or a pharmaceutically acceptable salt thereof, wherein $R^1$ is halogen, —$NR_2$, —OR, or an optionally substituted $C_{1-4}$ alkyl.

3. The compound according to claim 2 or a pharmaceutically acceptable salt thereof, wherein $R^1$ is $C_{1-4}$ alkyl.

4. The compound according to claim 3 or a pharmaceutically acceptable salt thereof, wherein $R^1$ is CH$_3$ or CH$_2$CH$_3$.

5. The compound according to claim 2 or a pharmaceutically acceptable salt thereof, wherein $R^1$ is halogen.

6. The compound according to claim 5 or a pharmaceutically acceptable salt thereof, wherein said halogen is fluoro or chloro.

7. The compound according to claim 2 or a pharmaceutically acceptable salt thereof, wherein $R^1$ is $NR_2$.

8. The compound according to claim 7 or a pharmaceutically acceptable salt thereof, wherein $R^1$ is NH$_2$, NHCH$_3$, N(CH$_3$)$_2$, NHCH$_2$CH$_3$, or NHCH$_2$Ph.

9. The compound according to claim 2 or a pharmaceutically acceptable salt thereof, wherein $R^1$ is OR.

10. The compound according to claim 9 or a pharmaceutically acceptable salt thereof, wherein $R^1$ is OCH$_3$ or OCH$_2$CH$_3$.

11. The compound according to claim 1, wherein one of -TR$^5$ is at the 3-position.

12. The compound according to claim 11, wherein -TR$^5$ is chloro, fluoro, —OH, optionally substituted $C_{1-4}$ alkoxy, —NHS(O)$_2$R$^a$, —S(O)$_2$NRR$^a$.

13. A compound selected from
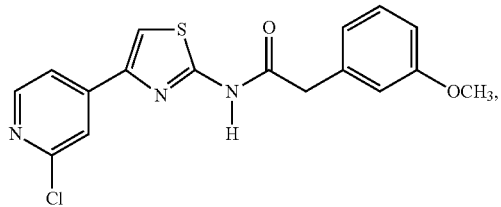
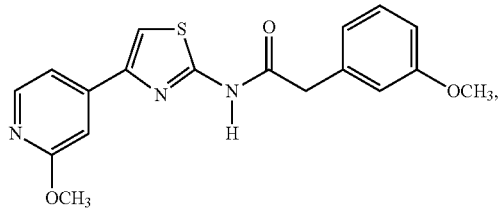
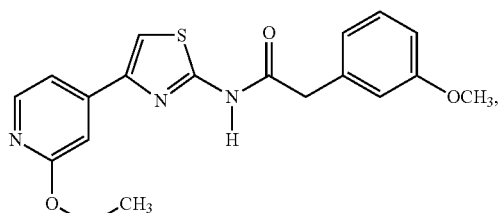
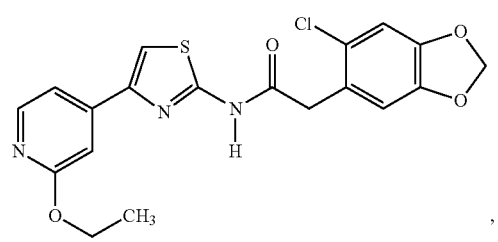
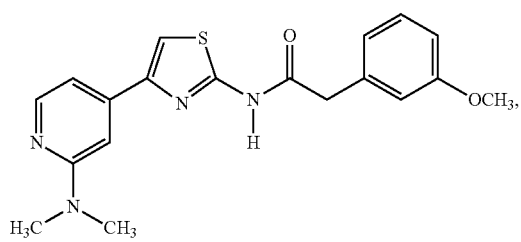
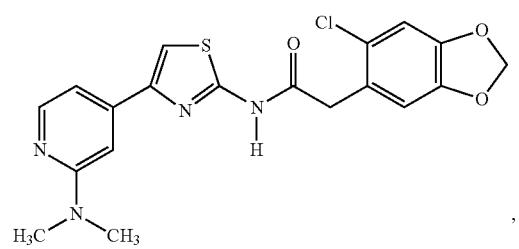
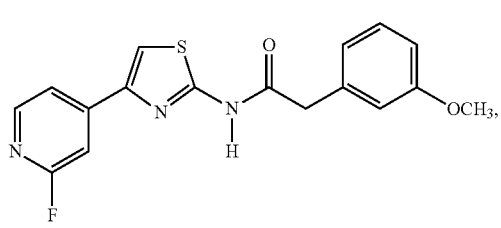
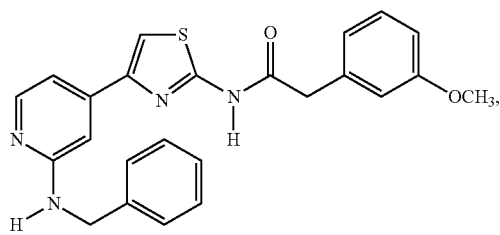
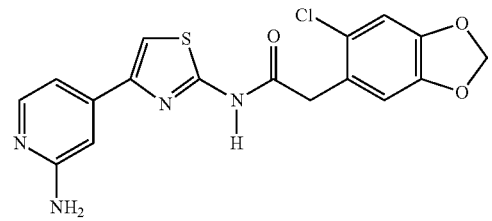
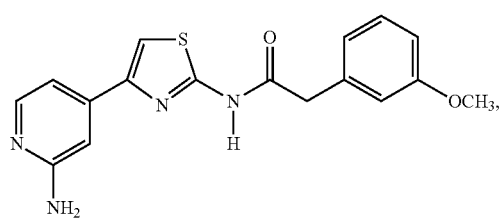
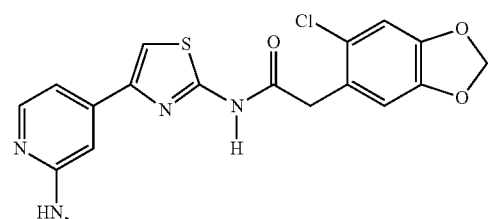
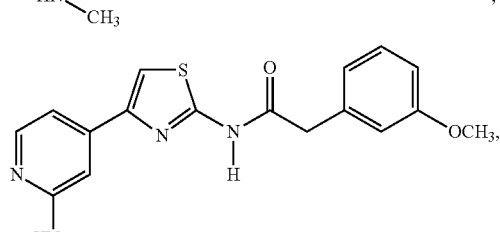
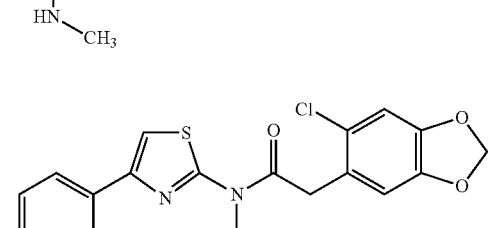
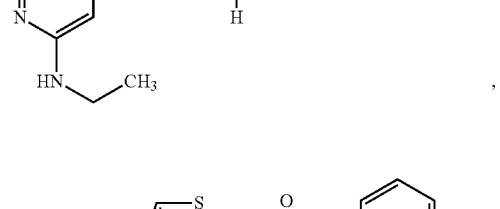

73
-continued
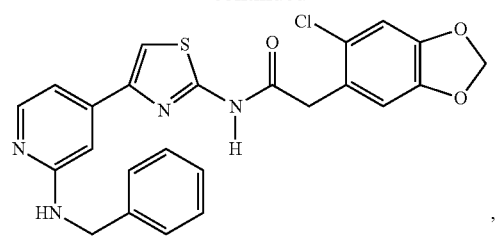
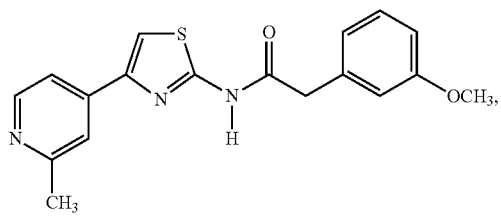
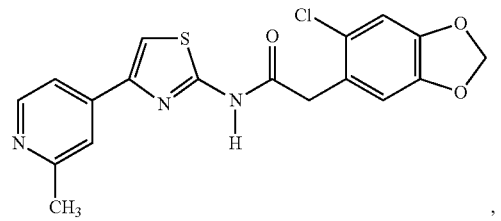
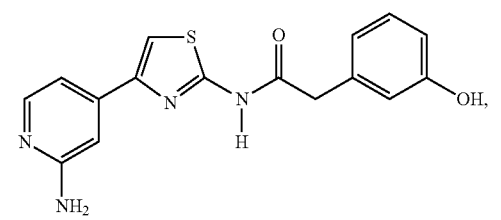
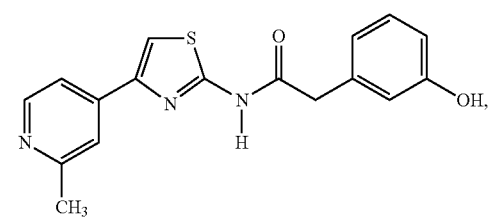
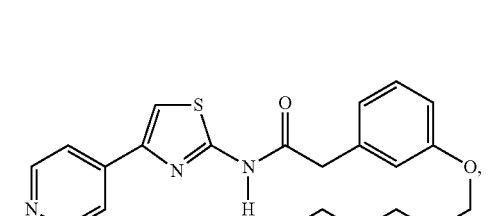
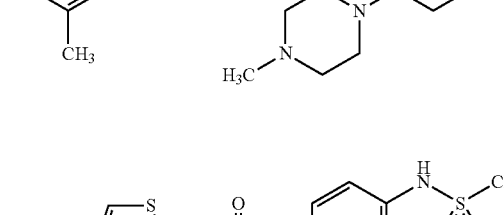
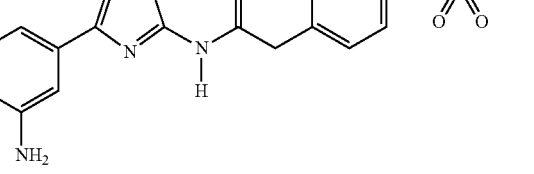
74
-continued
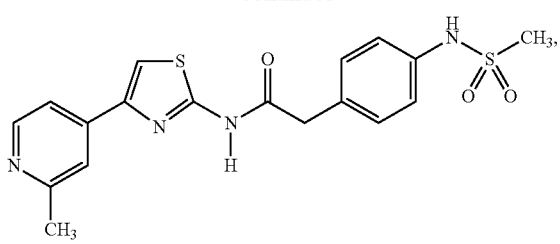
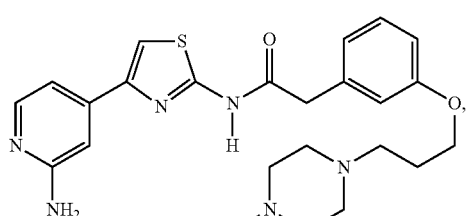
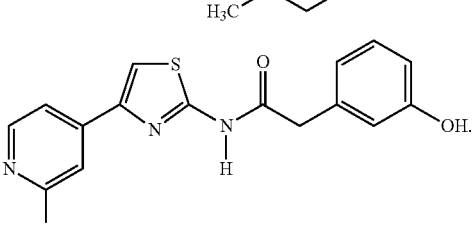
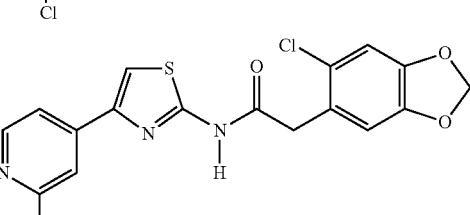
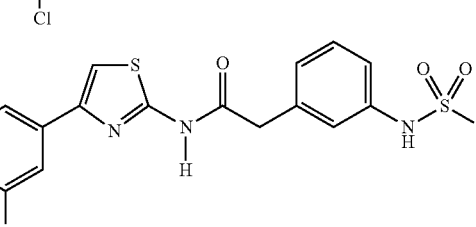
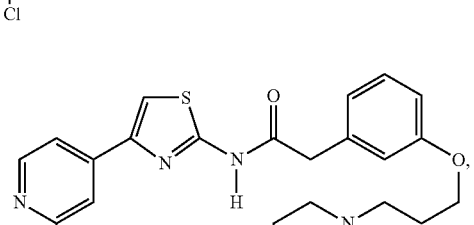
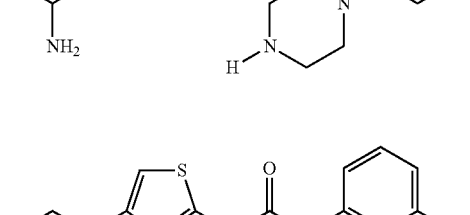
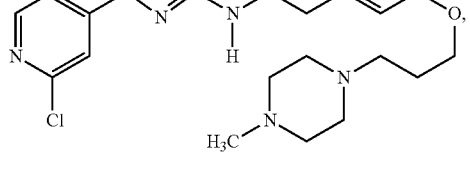

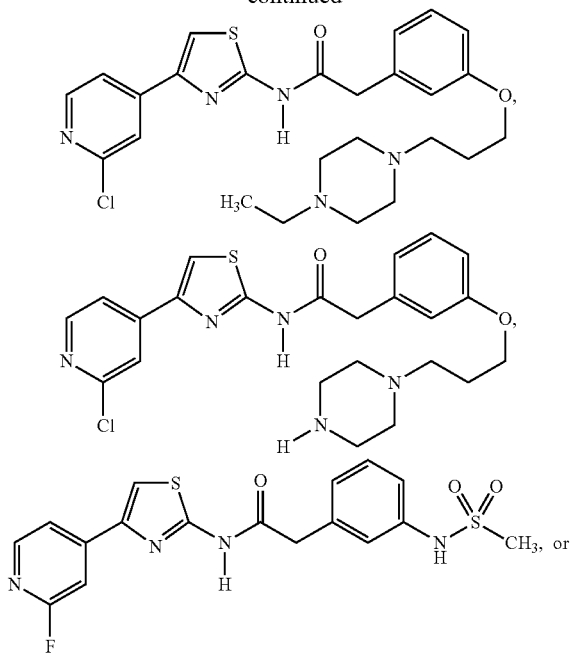

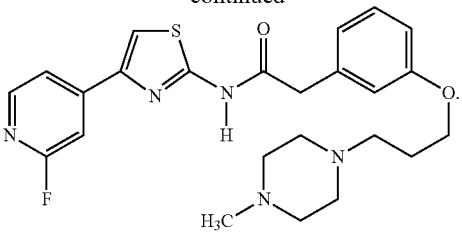

14. A composition comprising a compound according to claim 1 and a pharmaceutically acceptable carrier, adjuvant, or vehicle.

15. A method of inhibiting ROCK kinase activity in a biological sample comprising contacting said biological sample with a compound according to claim 1, or a pharmaceutical composition thereof.

16. A method of treating or lessening the severity of glaucoma in a patient comprising the step of administering to said patient a therapeutically effective dose of a composition according to claim 14.

* * * * *